(12) United States Patent
Taylor et al.

(10) Patent No.: US 6,453,906 B1
(45) Date of Patent: Sep. 24, 2002

(54) METHOD FOR FACILITATING THE DETACHMENT OF AN ARTERY AND THE LIKE

(75) Inventors: Charles S. Taylor, San Francisco, CA (US); Hani Shennib, Quebec (CA); Michael V. Morejohn, San Jose, CA (US)

(73) Assignee: CardioThoracic Systems, Inc., Santa Clara, CA (US)

( * ) Notice: Subject to any disclaimer, the term of this patent is extended or adjusted under 35 U.S.C. 154(b) by 90 days.

(21) Appl. No.: 09/625,397

(22) Filed: Jul. 26, 2000

Related U.S. Application Data

(60) Division of application No. 09/106,867, filed on Jun. 29, 1998, now Pat. No. 6,110,170, which is a continuation-in-part of application No. 08/835,675, filed on Apr. 10, 1997, now Pat. No. 5,871,496, which is a continuation-in-part of application No. 08/619,046, filed on Mar. 20, 1996, now abandoned.

(51) Int. Cl.⁷ .............................................. A61B 19/00
(52) U.S. Cl. ........................... 128/898; 606/49; 606/40; 606/159
(58) Field of Search .............................. 606/37, 41, 45, 606/48, 50, 190, 159; 128/898

(56) References Cited

U.S. PATENT DOCUMENTS

| | | | |
|---|---|---|---|
| 4,924,882 A | | 5/1990 | Donovan |
| 5,013,312 A | * | 5/1991 | Parins et al. .................. 606/37 |
| 5,324,288 A | | 6/1994 | Billings et al. |
| 5,542,945 A | | 8/1996 | Fritzsch |
| 5,676,662 A | | 10/1997 | Fleischhacker et al. |
| 5,718,703 A | | 2/1998 | Chin |
| 5,766,171 A | | 6/1998 | Silvestrini |
| 5,817,013 A | * | 10/1998 | Ginn et al. .................. 600/114 |
| 5,871,496 A | * | 2/1999 | Ginn et al. .................. 606/190 |
| 5,928,135 A | * | 7/1999 | Knight et al. ................ 600/104 |
| 6,110,190 A | * | 8/2000 | Ginn et al. .................. 606/190 |
| 6,280,455 B1 | * | 8/2001 | Ginn et al. .................. 606/190 |

FOREIGN PATENT DOCUMENTS

WO          WO 98/16162          *    4/1998

OTHER PUBLICATIONS

US 5,688,268, 11/1997, Billings (withdrawn)

* cited by examiner

Primary Examiner—Michael Peffley
(74) Attorney, Agent, or Firm—Fenwick & West, LLP

(57) ABSTRACT

A surgical instrument is configured to aid in performing a procedure of detaching an internal mammary artery (IMA) and the like, from the connecting tissues and side branch vessels which surround the artery in its native location, wherein the detaching procedure is preliminary to the performing of a coronary artery bypass grafting procedure and wherein the IMA is detached via a minimally invasive thoracotomy. To this end, an elongated slender rod includes a handle at its proximal end and an artery engaging loop, arc, fork configuration, or hook at its distal working end. Embodiments may incorporate electrosurgical capability or electrical insulation. A surgeon thus has means for harvesting an intact and undamaged graft vessel from its native location through a minimally invasive incision with enhanced speed, visibility, and freedom of motion.

5 Claims, 16 Drawing Sheets

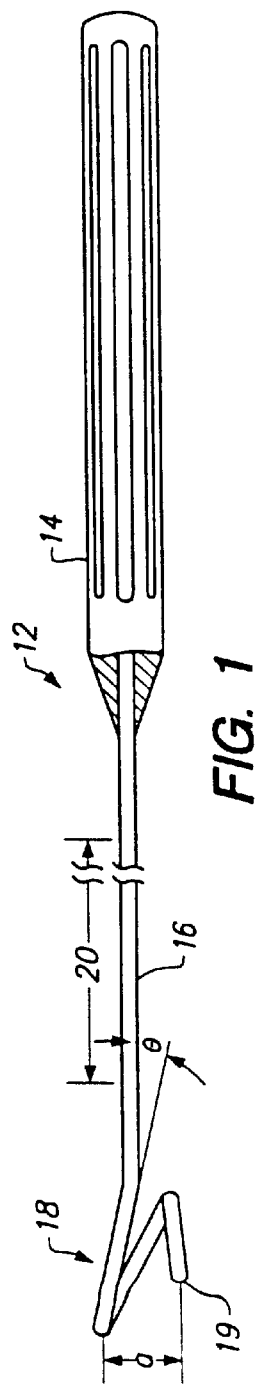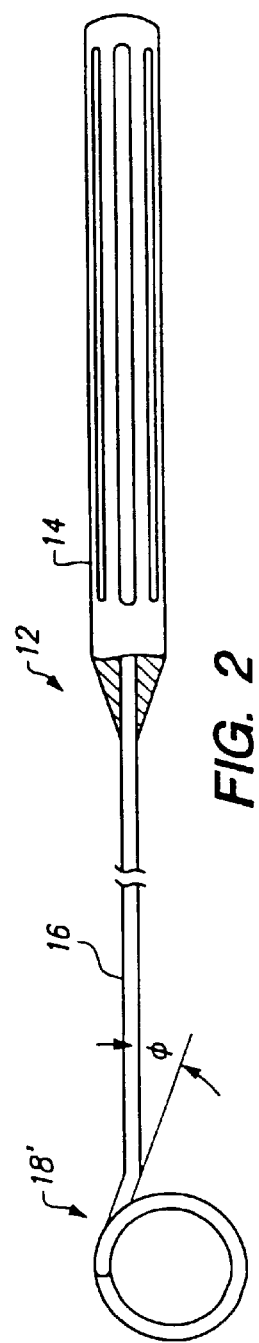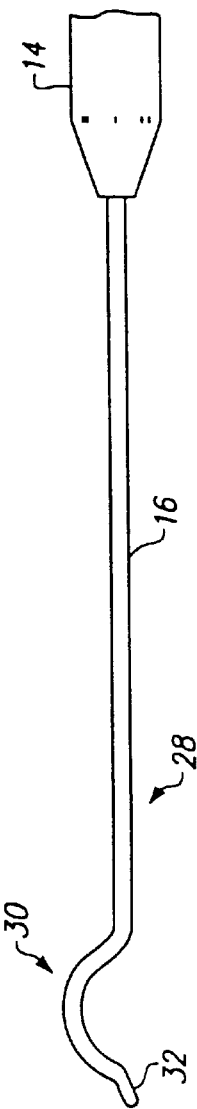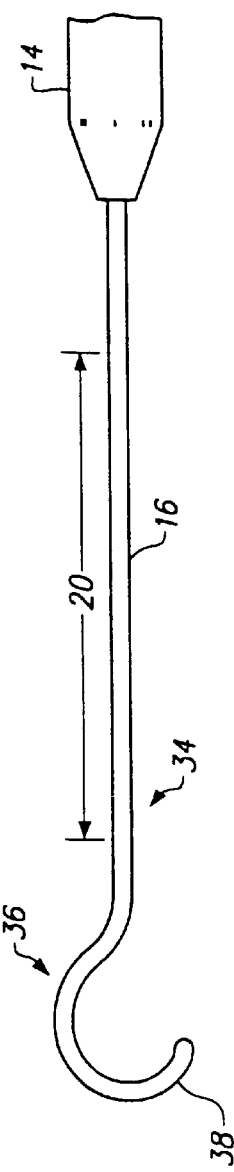

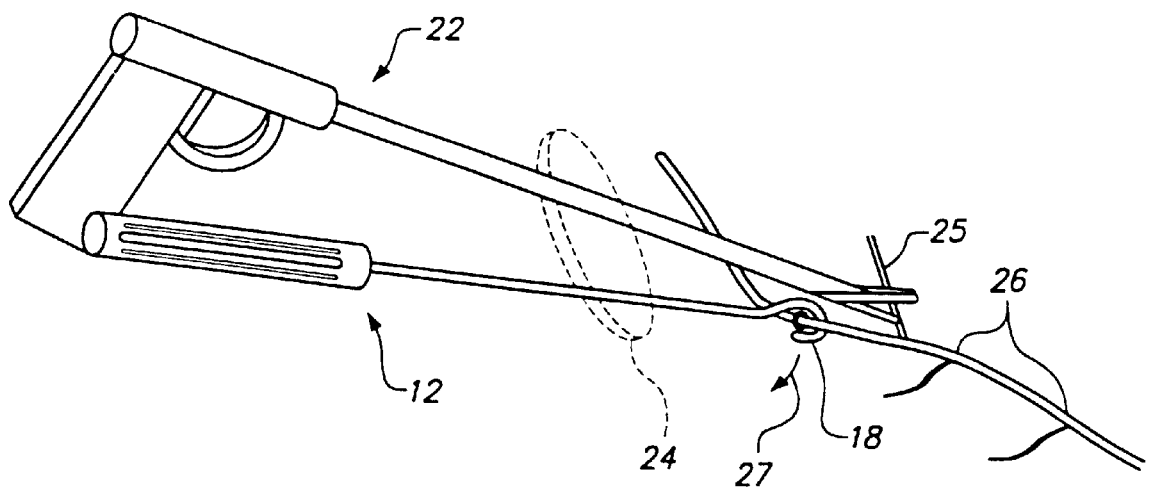
FIG. 3
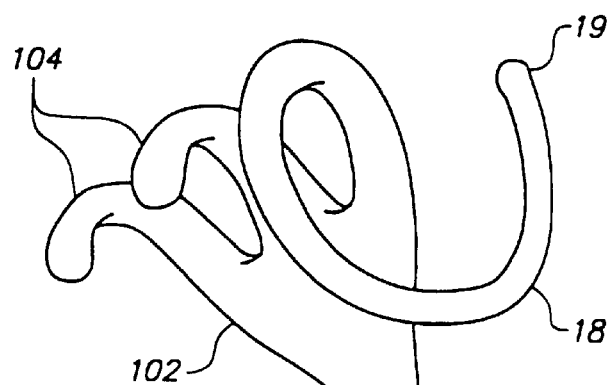
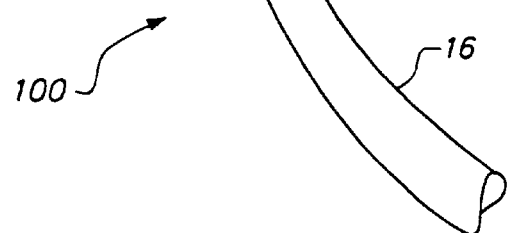
FIG. 10

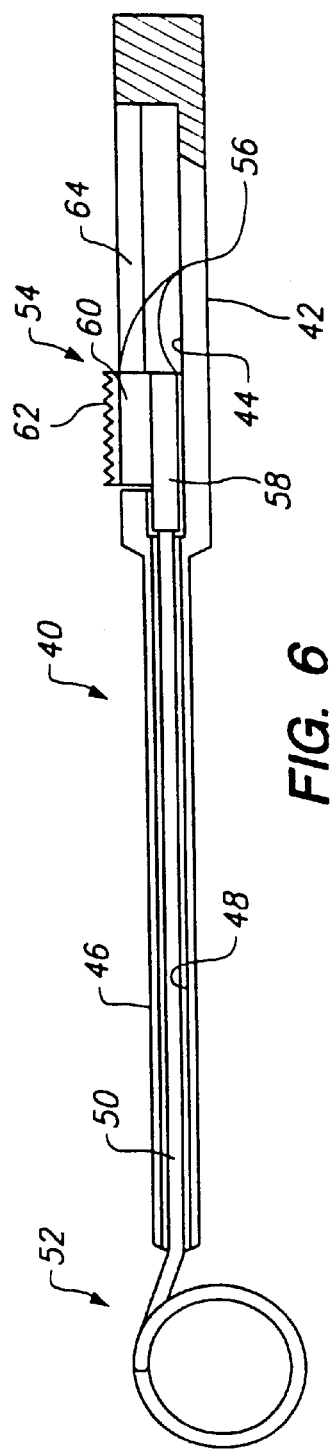
FIG. 6
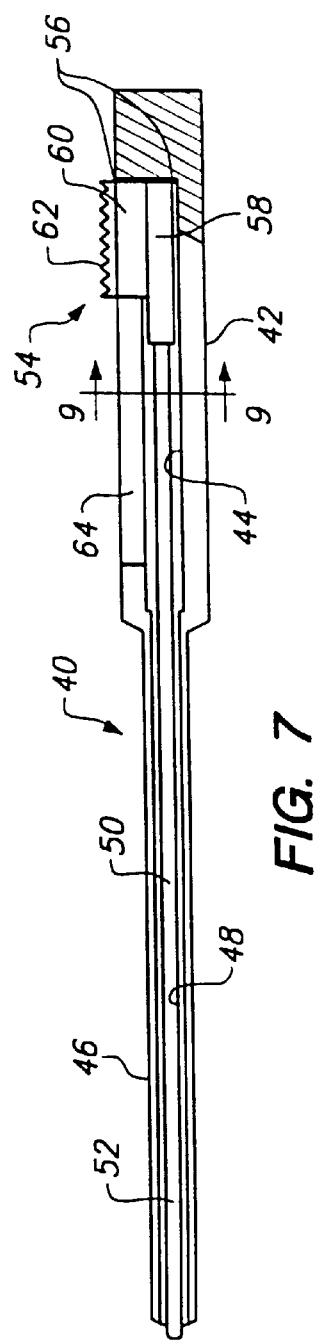
FIG. 7
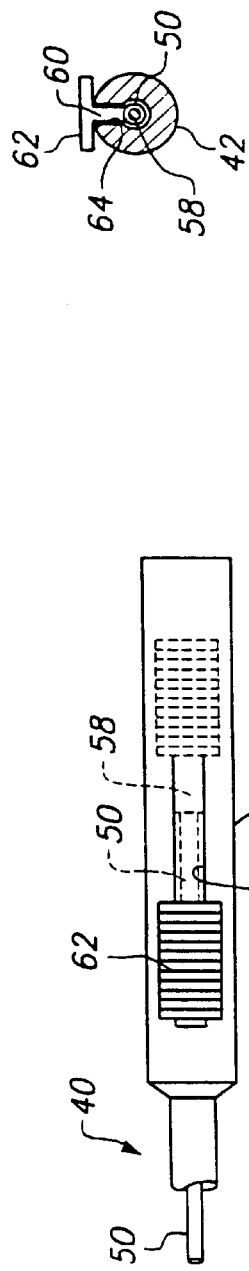
FIG. 9
FIG. 8

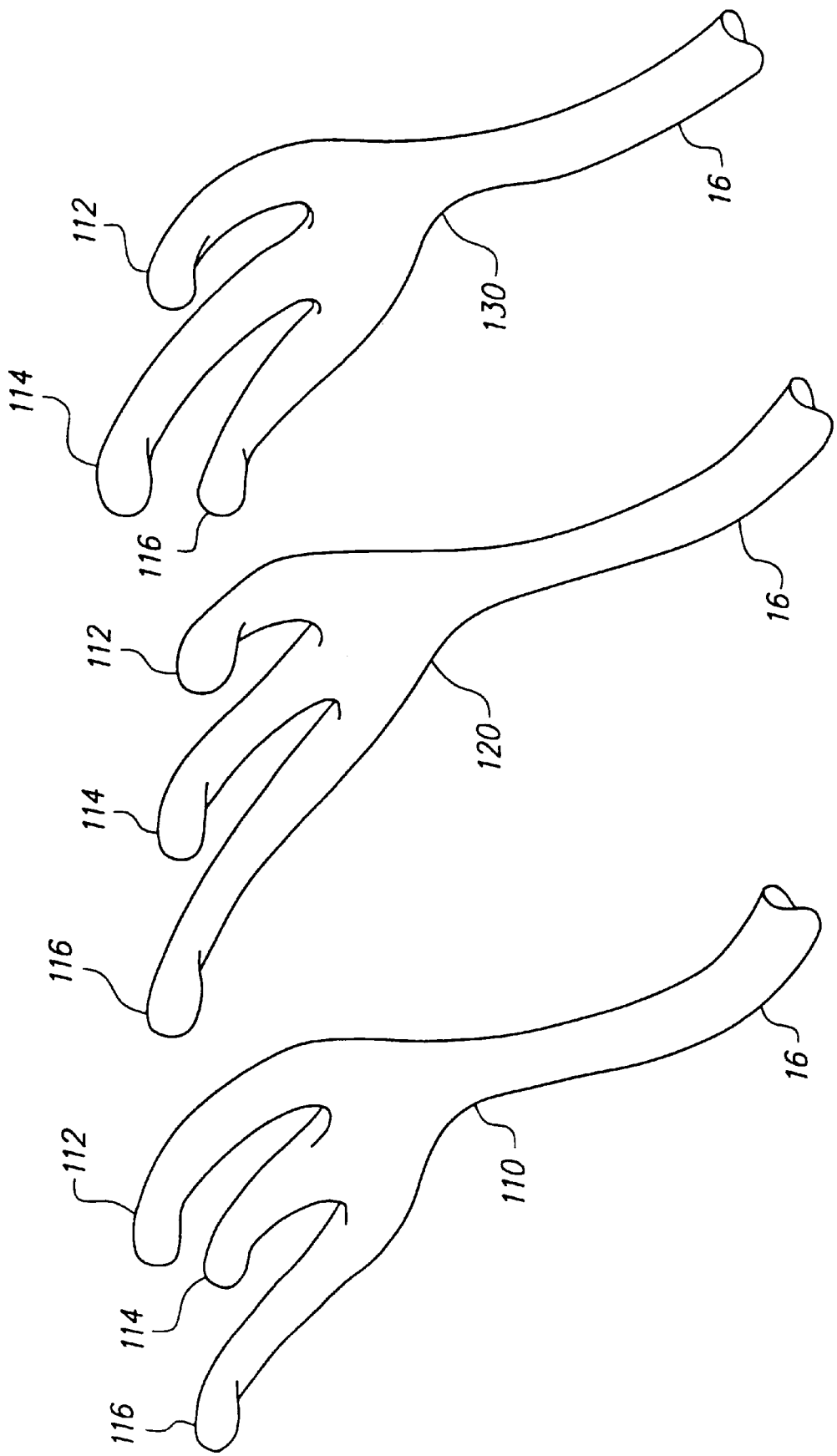

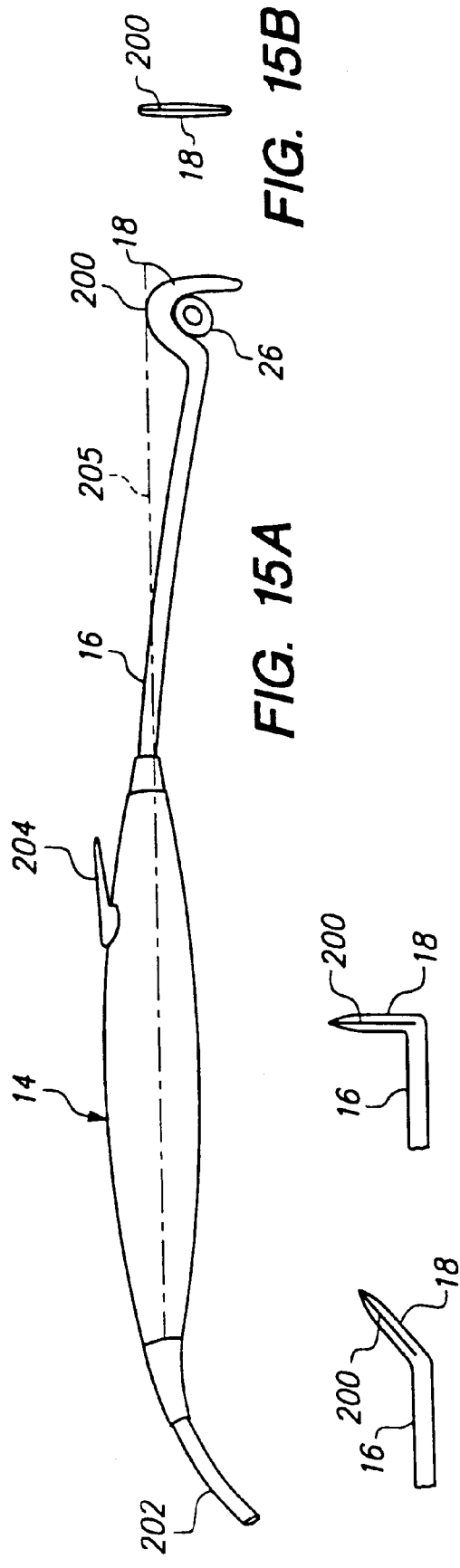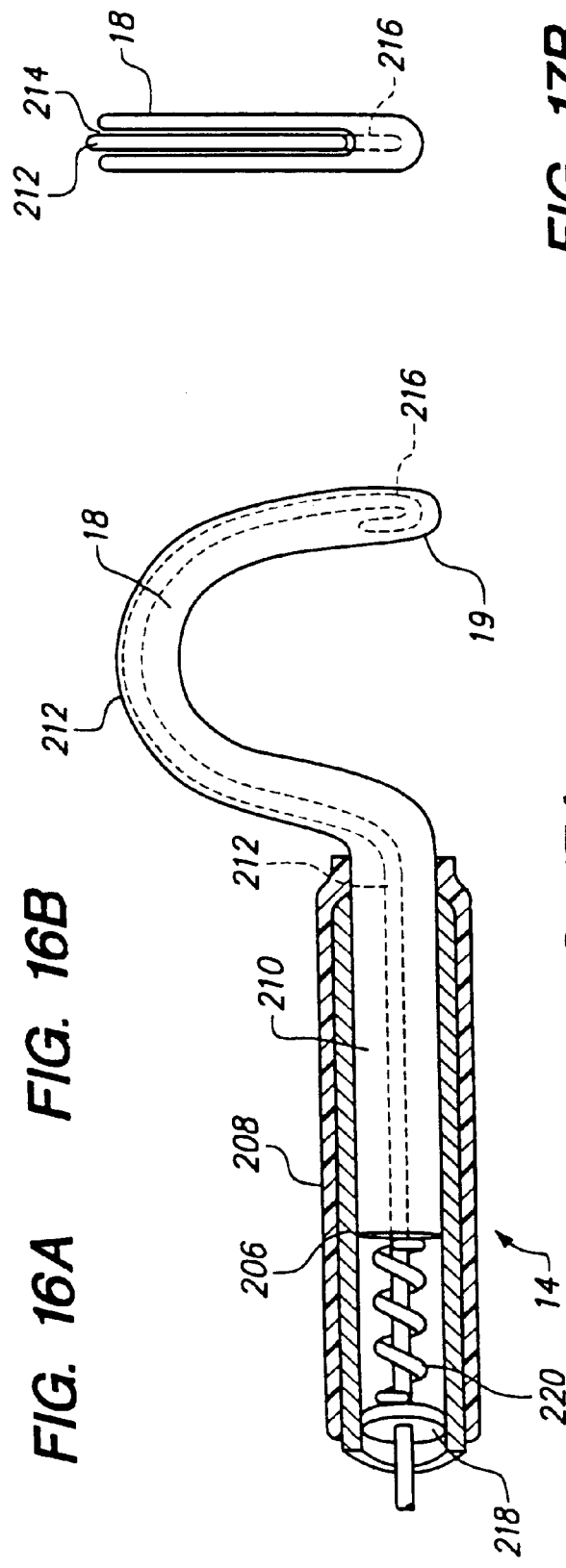

METHOD FOR FACILITATING THE DETACHMENT OF AN ARTERY AND THE LIKE

RELATED APPLICATIONS

This application is a divisional application entitled to priority from application Ser. No. 09/106,867, filed on Jun. 29, 1998, now U.S. Pat. No. 6,110,170, which is a continuation-in-part of co-pending application Ser. No. 08/835,675, filed on Apr. 10, 1997, which is a continuation-in-part of co-pending application Ser. No. 08/619,046, filed on Mar. 20, 1996, the disclosures of which are incorporated herein by reference as if set forth in full.

FIELD OF THE INVENTION

The present invention relates to minimally invasive surgical instruments and procedures and, in particular, to surgical tools for dissecting, manipulating and harvesting an artery, such as the internal mammary artery (IMA), from its natural location in connection with a coronary artery bypass grafting (CABG) procedure.

BACKGROUND OF THE INVENTION

Surgeons are constantly striving to develop advanced surgical techniques resulting in the need for advanced surgical devices and instruments required to perform such techniques. Recent advances in the surgical field are increasingly related to surgical procedures which are less invasive and reduce the overall trauma to the patient. To illustrate, in a conventional CABG procedure it has been common practice for surgeons to perform a sternotomy to expose the body cavity in the thoracic region. To this end, a surgeon makes a long incision down the middle of a patient's chest, saws through the length of the sternum and spreads the two halves of the sternum apart. Retractors then are employed to provide access to the vessels where an anastomosis will be performed. The CABG procedure is further complicated by the need to stop the beating of the heart by means of cardioplegia and to attach the patient to a cardiopulmonary bypass (CPB) machine to continue the circulation of oxygenated blood to the rest of the body while the graft is sewn in place.

To create a pedicled bypass graft, the surgeon dissects a sufficient length of the artery from its connective tissue, then transects the artery, and connects the transected end to a diseased target coronary artery distal to an obstruction, while leaving the other end of the dissected artery attached to the arterial supply, thus restoring blood perfusion to the heart.

The internal mammary arteries (IMAs), left (LIMA) and right (RIMA), are particularly desirable for use as pedicled bypass grafts as they are conveniently located, have diameters and blood flow volumes that are comparable to those of coronary arteries, and in practice typically have patency rates superior to other grafts such as saphenous veins from the patient's leg. Extending from the subclavian arteries near the neck to the diaphragm and running along the backside of the ribs adjacent the sternum, the IMAs deliver blood to the musculature of the chest wall. The LIMA is typically used as an arterial source for target locations on the left anterior descending coronary artery (LAD), the diagonal coronary artery (Dx), the circumflex artery (Cx), the obtuse marginal artery, and the ramus intermedius coronary artery. The RIMA is typically used for connection to all of the same target locations, as well as the right coronary artery (RCA) and the posterior descending artery.

Use of either IMA as a bypass graft first involves harvesting the IMA free from the inside chest wall. In conventional CABG approaches, access to the IMA is obtained through a sternotomy or major thoracotomy incision (involving sawing through one or more ribs) through the chest. Harvesting of the IMAs is accomplished with relative ease due to the working space made available by the sternotomy or major thoracotomy.

An IMA is detached from its connective tissue until there is sufficient slack in the IMA to allow the distal end thereof to be attached to the target vessel such as the left anterior descending coronary artery (LAD). The sternotomy incision provides the surgeon with ready access to the IMA since it is exposed by the spreading of the sternum. The IMA thus may be transected at its distal end and detached from the connective tissues in its native location in the sternum region, while still attached at its proximal end to its arterial supply, using the usual surgical instruments such as electrosurgical pencils, scissors, forceps, etc.

The CABG procedure would be improved if surgeons could avoid the need for arresting the heart, thereby eliminating the need to connect the patient to a cardiopulmonary bypass machine to sustain the patient's life. To this end, recent developments lend themselves to CABG procedures using surgical techniques which enable surgeons to perform the procedure while the heart is beating. This eliminates the need for the lengthy and traumatic cardiopulmonary bypass procedure, cardioplegia is unnecessary, the overall surgery is much less invasive and traumatic, and patient recovery time and costs are reduced. Recently, progress has been made in advancing minimally invasive surgical techniques, particularly in cardiothoracic surgery, which eliminates the need for a sternotomy or major thoracotomy. Access to the heart with these minimally invasive techniques is obtained through one very small surgical incision (such as a minimal thoracotomy) or through several percutaneous cannulas known as trocars positioned intercostally in the thoracic cavity of the patient Visualization of the operative area may be facilitated by thoracoscopes which typically consist of a video camera configured for introduction through a small incision or trocar to allow observation of the target area on a video monitor.

With the advent of these minimally invasive techniques, harvesting the IMA has become more complex and difficult due to a restricted work space and access, and to reduced visualization of the IMA. The procedure of detaching the IMA likewise must be performed through the minimal thoracotomy. Surgeons presently perform the procedure of detaching the IMA from its native location with the aid of the usual instruments such as the electrosurgical pencils, scissors and forceps of previous mention. These instruments are not specially designed for use in less invasive procedures and do not facilitate the desired gentle handling of the IMA as it is detached from the surrounding connective tissues to provide the bypass graft for the CABG procedure. The harvesting procedure itself may actually be lengthened and the trauma to the vessel potentially increased by the less invasive techniques, in part because a number of tools must be introduced and exchanged through the restricted incision (s). This is a concern as a high degree of precision is required when harvesting a bypass vessel to avoid injury (such as over cutting or cauterizing) to the vessel which may in turn lead to increased rates of occlusion in the vessel in the months and years after the procedure.

Although low-profile micro-surgical instruments are readily available for some procedures, such has not been the case for harvesting the IMA and other similarly situated arteries in minimally invasive CABG procedures. Surgical instruments designed for laparoscopic and other minimally invasive applications are not generally suitable for performing minimally invasive CABG. Most laparoscopic procedures, for example, target body structures which are quite large in comparison to coronary vessels, and do not require the high degree of precision required in a CABG procedure. Accordingly, laparoscopic instruments generally provide only limited angular orientation, making them unsuitable for harvesting of the IMA and other similarly situated arteries through a minimal thoracotomy or an intercostal puncture site.

Typically, an electrosurgical tool (often called a "Bovie") similar to that described in U.S. Pat. No. 5,013,312 is used to free a length of the IMA by incising the endothoracic fascia and severing the side branch vessels to free the IMA. The use of such electrosurgical devices is well known in the art and can be crucial in controlling bleeding during harvesting of the IMA. Such devices are typically in the form of scalpels, forceps, and scissors, and employ at least one conductive electrode connected thereto. For example, a bipolar electrosurgical instrument comprising a fork-shaped configuration is described in U.S. Pat. No. 4,671,274. This instrument combines the functions of tissue manipulation and electrocautery, and finds application for control of bleeding during the transection of blood vessels; however, it involves separate hinged jaws and cannot provide an adequate range of angular motion through a minimally invasive thoracotomy.

Despite the use of an electrosurgical tool, because initial cauterization may be applied over too short a length of a vessel or side branch to be complete, it is common practice to apply ligatures or surgical clips to control bleeding before complete coagulation is effected. Applying ligatures or clips can be time-consuming. In addition, if clips are accidentally loosened and dropped inside the patient's body cavity, there can be serious complications and additional expenditure of time in the procedure.

When an electrosurgical tool is used in simultaneous conjunction with other instruments that are not electrically insulated, there is a serious risk of accidental electric short-circuiting or arcing due to contact or close proximity. This can lead to traumatic electric shock to the patient or the surgeon, damage to an instrument, disruption of the procedure, or over or under cutting or cauterization, which can adversely affect the control of bleeding or the integrity and patency of the graft vessel.

Accordingly, it would be highly desirable when performing a detachment, or "takedown" procedure on the IMA, to provide a specialized instrument which allows the surgeon a greater range of visibility and angular motion to harvest an intact and undamaged length of vessel more rapidly and gently with fewer instruments obstructing the operating field and with minimal risk of accidental electric shock, while the tissues and side branch vessels are being dissected with the aid of a surgical knife or scissors. It would further be desirable to reduce or eliminate the need for surgical clips or sutures in the IMA harvest procedure.

SUMMARY OF THE INVENTION

The present invention provides a specialized surgical instrument which overcomes the deficiencies of previous mention, that is, provides gentle handling of the IMA when performing the procedure of detaching the IMA from its native location during the less invasive CABG procedure using the comparatively small incision or thoracotomy in the chest. It potentially reduces the number of instruments obstructing the field and, in some embodiments, provides malleable instrument shafts, thereby allowing the surgeon a greater range of visibility and angular motion to harvest an intact and undamaged length of vessel more rapidly. It provides electrically insulated instruments and self-contained electrosurgical instruments that reduce the risk of accidental electric shock. It provides embodiments that potentially reduce the need for surgical clips or sutures to control bleeding. These advantages are also applicable to the dissection or harvesting of other vessels for use as a graft in a vascular surgical procedure.

More particularly, in selected embodiments the invention comprises an elongated slender rod, permanently attached to a handle of greater cross section configured for comfortable grasping by a surgeon. The slender rod may be formed of a material such as a firm plastic, but preferably is formed of stainless steel. The distal end of the rod is formed into a loop or coil, an arcuate segment or other preselected curved configuration which provides means for capturing the IMA, or other vessel, which is being detached, dissected or otherwise handled. Some of the various embodiments contemplated by the invention include a full 360 degree loop configuration with the overlapped coil of the loop axially spaced apart, as well as partial loop and arcuate configurations. The distal, or working, end of the invention is configured and is of selected dimensions to allow a surgeon to capture a vessel at a distant location through small openings in a patient's body, and to then gently manipulate the vessel as necessary in the specific surgical procedure. Thus, the invention provides the advantage of remotely handling a vessel with a minimum of trauma during minimally invasive surgical procedures.

In alternative embodiments, the invention includes an elongated tube coaxially attached to the handle, and a rod actuating means integral with the handle. In response to the rod actuating means, the rod and the integral working end is extended from the distal end of the tube as when in use, or may be retracted into the tube when not in use.

In further alternative embodiments, the invention includes a fork configuration that can engage and manipulate a vessel and connective tissue. These embodiments facilitate safe and rapid severing of the many side branches that must be separated from the main vessel, with minimal bleeding or damage to the harvested vessel. Described configurations protect the harvested vessel from accidental damage by an electrosurgical knife. Instruments according to the invention are coated with electrically insulating material to prevent accidental shortcircuiting and arcing when used with electrosurgical tools. Other embodiments incorporate selfcontained unipolar or bipolar electrosurgical capabilities, thereby eliminating the need for extra instruments, potentially reducing or eliminating the need for surgical clips or sutures to control bleeding, and improving the accuracy, speed, and safety of vascular graft dissection.

In still other alternative embodiments, the invention includes an electrically energized cautery wire, coil, ribbon, etc., selectively embedded or otherwise contained in a loop, hook, or other curved configuration used to capture the vessel. The cautery element incorporated in the curved configuration provides an electrosurgical instrument that not only can engage and gently manipulate a vessel, or other elongated bodily structures and connective tissue, but which also can be used to rapidly sever and cauterize side branches of the vessel and separate the vessel and the tissue around it from their native bed. This is turn eliminates the need for extra instruments and for surgical clips or sutures. The cautery means may be unipolar or bipolar and the embodiments may include selected fiberoptic light and/or smoke evacuation means in the region of the curved configuration to enhance visualization of the vessel. The body of the curved configuration, that is, the insulated cross-section thereof, acts as a spreading means, applying tension to the tissue to be divided by the cauterizing member, i.e. cautery element, and insulates the nearby tissue, and most importantly the vessel itself, or other elongated bodily structure or tissue, from the electrosurgical action and heat of the cautery element.

BRIEF DESCRIPTION OF THE DRAWINGS

FIGS. 1 and 2 are top and elevational views, respectively, of an embodiment of the present invention.

FIG. 3 is a perspective view illustrating a use of the invention in cooperation with surgical scissors when performing the procedure of detaching the IMA from its native location.

FIGS. 4 and 5 are elevational views of alternative embodiments of the invention.

FIGS. 6 and 7 are elevational views of a further alternative embodiment of the invention embodying a retractable distal working end.

FIG. 8 is a partial top view of the embodiment of FIGS. 6, 7.

FIG. 9 is a cross-sectional view taken along section line 9—9 of FIG. 7.

FIG. 10 shows an embodiment combining a loop with a fork configuration.

FIGS. 11A–11C illustrate fork configurations having fingers of unequal lengths.

FIGS. 15A and 15B are elevational and end views respectively, illustrating a further embodiment including a curved or hooked configuration containing exposed cautery wire means as an electrode for severing and cauterizing side branches and connective tissue.

FIGS. 16A and 16B are top views of alternative curved or hooked configurations of FIGS. 15A, 15B.

FIGS. 17A and 17B are elevational and end views respectively of the exposed cautery wire means of FIGS. 15A, 15B.

DETAILED DESCRIPTION OF THE EMBODIMENTS

Figure 12:
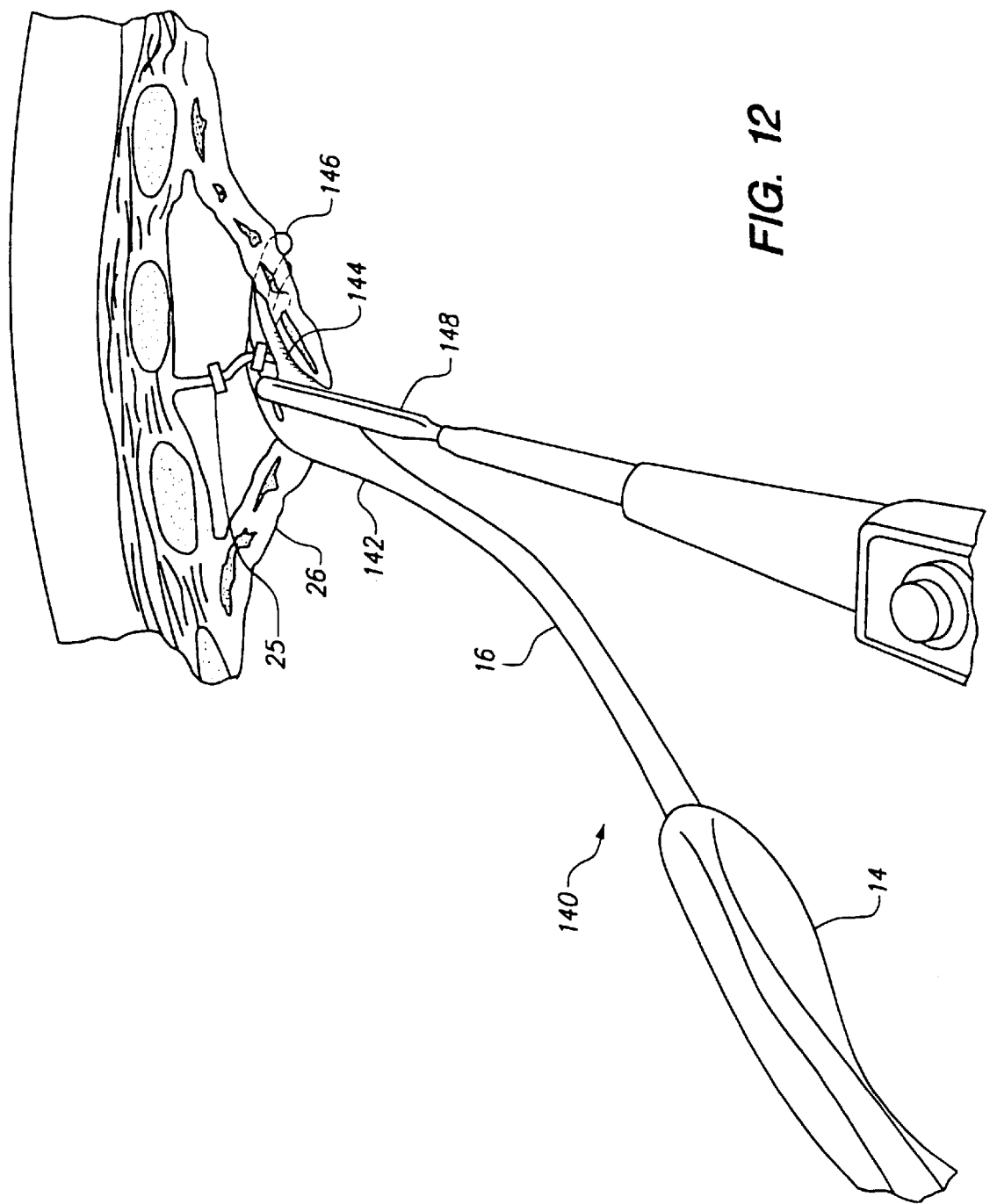
FIG. 12 is a perspective view showing a use of the invention including a fork configuration to assist in detaching the IMA.

FIGS. 1 and 2 illustrate one embodiment 12 of a surgical instrument in accordance with the present invention, which includes a handle 14 at the proximal end securely attached to, or formed as part of, an elongated slender rod 16. Rod 16 may have a circular, oval, rectangular, triangular or other cross-sectional shape over all or any portion of its length, and may be solid or hollow in whole or in part, containing one or a plurality of internal cavities. The distal end of the instrument, and particularly of rod 16, is formed into a loop 18. The loop 18 may be continued to form a complete circle as depicted in FIGS. 1 and 2, or may be of less than a full circle, such as exemplified by the arcuate embodiments depicted in FIGS. 4 and 5 below. Loop 18 has an inside diameter of the order of one-half to three-quarter inch, and the overlapping tip 19 of the loop is spaced from the body of the loop a distance, a, of the order of one-fourth to one-third inch. Preferably, the circumference of loop 18 does not lie in a single plane but is displaced helically to provide axial displacement between separate points on the loop. As depicted in the figures by way of example only, loop 18 is bent at an angle relative to rod 16 of approximately 10 degrees in the top view (FIG. 1), and at an angle of approximately 20 degrees in the elevational view (FIG. 2). Rod 16 and handle 14 may be formed in whole or in part of stainless steel, aluminum, or plastic, respectively. If a combination of materials is used, the rod is bonded or glued to the handle via a suitable axial bore in the handle. It may be preferable for use in electrosurgical procedures that the instrument be non-conductive electrically; accordingly, if rod 16 (and/or handle 14) is formed of stainless steel or other electrically conductive material, it may be coated with a non-conductive biocompatible material such as PTFE or polyamide polymer. Rod 16 and handle 14 also may be made of any of the other conventional biocompatible medical plastics having sufficient tensile and bending strength.

In a preferred embodiment, rod 16 is formed of a stainless steel material and thus is relatively resistant to force applied transversely to the rod length. However, a partial length 20 (FIG. 1) of rod 16 may be annealed to have a malleable property, whereby rod 16 can be deformed by the surgeon to tailor the precise curvature thereof depending on the nature of the procedure, the patient's anatomy, and the preferences of the surgeon. Loop 18 can likewise be annealed in whole or in part to have a malleable property.

FIG. 3 illustrates a manner of use of the invention employing the embodiment 12 of FIGS. 1 and 2. It is to be understood that any of the embodiments presented herein also may be used in similar fashion to perform the same function. To this end, surgical scissors 22 may be introduced by a surgeon through a thoracotomy 24 and used to initiate the severing of tissues from a vessel such as an IMA 26 to thus initiate detachment of a first segment of the IMA. In the following description, the IMA is used as the example, with the understanding that other vessels may be harvested using the devices and procedures of the invention. Upon slight detachment of the IMA, instrument 12 of the invention also is inserted through the thoracotomy 24 and the tip 19 of loop 18 is introduced past IMA 26. A slight twist of instrument 12 causes loop 18 to encircle the IMA whereupon the surgeon has complete control of the direction in which force may be applied to urge the IMA gently from its native location. Scissors 22 simultaneously are used to dissect tissues and side branch vessels 25 from the IMA. The surgeon may continue the procedure of dissecting the connecting tissues and side branch vessels while pulling the IMA away from the endothoracic fascia with instrument 12 as depicted by arrow 27, until a sufficient length of the IMA has been detached from the endothoracic fascia to allow performing a CABG procedure. The invention thus allows capturing the IMA and provides the surgeon thereafter with complete control of the artery to allow it to be manipulated gently in any direction during the detaching process.

FIG. 4 illustrates an alternative embodiment 28 of the invention, wherein the full loop 18 of the FIGS. 1 and 2 is defined by one or more arcuate segments, which comprise at least one arc 30 formed in the distal end of rod 16. Arc 30 terminates in a tip 32 which is bent away from the arc configuration to extend generally coaxially with rod 16. Tip 32 guides the introduction of arc 30 through the surrounding tissues and past the IMA, whereby arc 30 is used to manipulate the IMA while detaching it from the endothoracic fascia.

FIG. 5 illustrates a further alternative embodiment 34 of the invention, wherein the loop 18 of FIGS. 1 and 2 is defined by a slightly ovaled partial loop 36 of approximately three-fourths of a full oval or circle. This configuration provides a tip 38 which allows manipulating the IMA in various directions without completely encircling the artery as with loop 18. As depicted in FIG. 5, rod 16 may be annealed along a length 20 as described in FIG. 1, to allow readily deforming the rod to tailor the contour of the instrument to meet the requirements of the procedure, the anatomy of the patient, and the preferences of the surgeon to facilitate the capture and manipulation of the IMA by loop 18, arc 30 or partial loop 36.

FIGS. 6–9 depict portions of alternative embodiments 40 of the invention employing a retractable distal working end of the instrument. Rod 16 and loop 18 (or arc 30 or partial loop 36) may be retracted into a protective housing when not in use, and extended to provide loop 18 when the instrument is to be used. Instrument 40 includes a hollow handle 42 having thus a lumen 44. An elongated tube 46 is coaxially formed with the handle 42 and includes a lumen 48 extending the length of the tube 46 in communication with lumen 44. A slender elongated rod 50 similar to rod 16 of FIGS. 1, 2, 4, and 5 is dimensioned to fit in slidable relation within lumen 48 of tube 46. Rod 50 is formed, for example, of a nickel-titanium alloy material having an inherent shape-memory property. In this embodiment the distal working end of rod 50 is formed into a loop 52 similar to the loop 18 of FIGS. 1 and 2, which thus is the shape to which the shape-memory material, that is, the distal working end of rod 50, will return. It is to be understood that the distal working end of rod 50 could be formed into the arcuate or partial loop configurations of FIGS. 4 or 5, respectively, rather than the full loop configuration 18, 52. FIG. 6 depicts instrument 40 with rod 50 extended to provide an exposed vessel capturing distal working end for use by a surgeon.

FIG. 7 depicts the instrument 40 with rod 50 retracted into tube 46. As may be seen, the shape-memory material is sufficiently flexible that, when rod 50 is drawn into lumen 48 of tube 46, loop 52 is forcibly deformed to assume the shape of the lumen, that is, loop 52 is straightened. Thus, the working end of the instrument may be fully retracted into the protective housing of tube 46. When the instrument is to be used in a procedure of detaching a vessel such as the IMA from its connecting tissues, rod 50 is extended from tube 46, whereupon due to the inherent shape-memory property of the nickel-titanium alloy material, loop 52 will automatically re-form into its memorized shape depicted in FIG. 6.

Various mechanical devices may be employed with handle 42 to provide rod 50 with working end 18, 30, 36 operated by an actuating means 54. By way of example only, actuating means 54 herein includes a reciprocatable slide 56 formed with a cylindrical member 58 slidably fitted within lumen 44 of handle 42. Cylindrical member 58 is integrally formed with a radially-extending flat yoke 60 which, in turn, has a thumb-engaging member 62 secured thereto. Flat yoke 60 reciprocates within a slot 64 formed in the side wall of handle 42 in communication with lumen 44, and thumb-engaging member 62 is positioned exterior of slot 64 and outer cylindrical surface of handle 42 for access by the surgeon's thumb or fingers. Rod 50 is coaxially secured to cylindrical member 58 and thus any reciprocation of thumb-engaging member 62 imparts similar reciprocation to rod 50.

Although slidable actuating means 54 is illustrated herein, other mechanisms may be used. For example, the proximal end of rod 50 may be provided with external helical threads, wherein a coaxial circular dial with internal matching helical threads is disposed within the distal portion of handle 42 with the internal threads engaging the external threads. Selective rotation of the dial thus reciprocally translates rod 50 to extend or retract the rod and working end of instrument 40.

Figure 13:
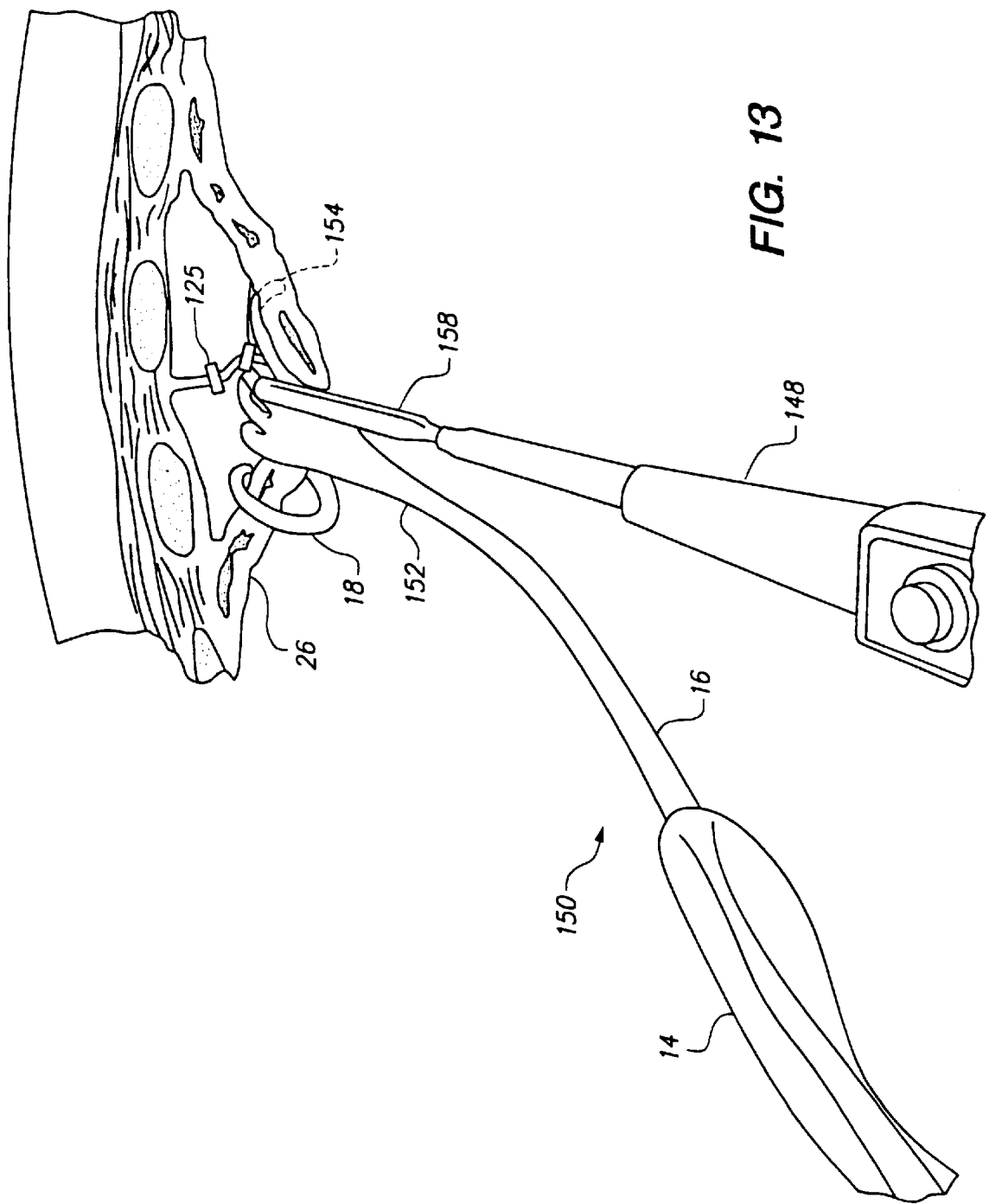
FIG. 13 is a perspective view illustrating the use of the invention including a fork configuration combined with a loop to assist in detaching the IMA.

An alternative preferred embodiment of the invention comprising a fork configuration at the distal working end of rod 16 is illustrated in FIGS. 10, 11A–11C, 12, 13, and 14. The fork configuration may be combined with loop 18 as depicted in FIGS. 10 and 13 or with arcuate configuration 30 or partial loop configuration 36 shown in FIGS. 4 and 5 respectively; alternatively a fork configuration may be used in place of loop 18 or equivalents at the distal working end of rod 16. It is to be understood that a fork configuration may be combined with malleable rod section 20, handle 14, retractable rod 50, hollow handle 42, actuating means 54, or any other element described herein.

Proceeding, FIG. 10 illustrates an embodiment 100 in which fork configuration 102 and loop 18 are combined at the distal working end of rod 16. Fork configuration 102 comprises a plurality of fingers 104 projecting from the distal end of the fork configuration. For purposes of illustration a finger 104 is formed into a arcuate or circular configuration, such as loop 18, terminating in tip 19. The diameter of the loop portion 18 of finger 104 may be slightly tapered from its proximal connection point to tip 19. Preferably, loop 18 is between about 270? and 360?. Tip 19 and the tips of fingers 104 preferably end in a bulbous configuration or have a tear drop shape. Fork 102 may comprise at least two and up to any greater number of fingers 104, one or more of which may be formed into a loop or equivalent, depending on the detailed design of embodiment 100. Likewise the lengths, widths, and spacing of fingers 104 may be chosen to be equal or unequal in any order at the discretion of the instrument designer. Fingers 104 may be straight, bent, curved, or adjustably shaped at the discretion of the designer.

FIGS. 11A–11C illustrate fork configurations at the distal working end of rods 16 having fingers of unequal lengths. FIG. 11A shows a fork 110 having inner finger 114 shorter than outer fingers 112 and 116. FIG. 11B shows a fork 120 in which left-hand outer finger 112 is shortest, inner finger 114 is intermediate in length, and right-hand outer finger 116 is longest. FIG. 11C shows a fork 130 having inner finger 114 longer than outer fingers 112 and 116. Preferably, any two adjacent fingers define a rounded "V"-shape groove to accommodate vessels of varying diameters for scraping or dissecting tissue away from a vessel.

FIG. 12 illustrates a manner of use of the invention employing an embodiment 140 comprising a fork configuration 142. In the illustrated embodiment a fork 142 is connected to the distal working end of rod 16, which is fastened to handle 14. Fork 142 comprises fingers 144, which terminate at their distal ends in enlarged hemispherical or rounded tips 146. Tips 146 are configured to make gentle atraumatic contact with a patient's tissue. In the illustrated procedure fork 142 gently captures, retracts, and stabilizes IMA segment 26 or other tubular organ away from its connective tissue. The IMA and/or separated and clipped side branch and tissue 25 may be captured and woven between fingers 144 to provide additional control and stability. Combination of a malleable rod 20 (FIG. 1) and adjustable finger shapes provide the surgeon with a wide range of angular motion through a small minimally invasive incision. An electrosurgical knife 148, such as a "Bovie" or such as that described in U.S. Pat. No. 5,013,312, may then be employed by the surgeon to coagulate and cut offside branch 25 from IMA 26. Fingers 144 provide a sliding guide surface for knife 148 to cut offside branch 25 cleanly and accurately, and protect IMA 26 from accidental injury by the knife. Instrument 140 positions, stabilizes, and protects IMA 26 during the described dissection procedure, reducing the time and risk of the procedure.

FIG. 13 illustrates a manner of use of the invention employing an embodiment 150 comprising a fork configuration 152 combined with loop 18 at the distal working end of rod 16 affixed to handle 14. In the illustrated procedure loop 18 captures and gently stabilizes IMA 26. Fingers 154 of fork 152 are curved to engage and retract IMA 26 and to separate side branch 25 between fingers 154. The surface defined by adjacent fingers 154 protects IMA 26 and provides a sliding support to guide electrosurgical knife 148 to coagulate and cut offside branch 25 quickly, accurately, and safely, reducing the time and risk of the procedure. Embodiment 150 illustrates the cooperative action between fork 152 and loop 18, wherein the loop controls IMA 26, while the fork captures side branch 25 and guides knife 148. This functionality potentially reduces the need for extra instruments in the small operating field.

Figures 14, 18A:
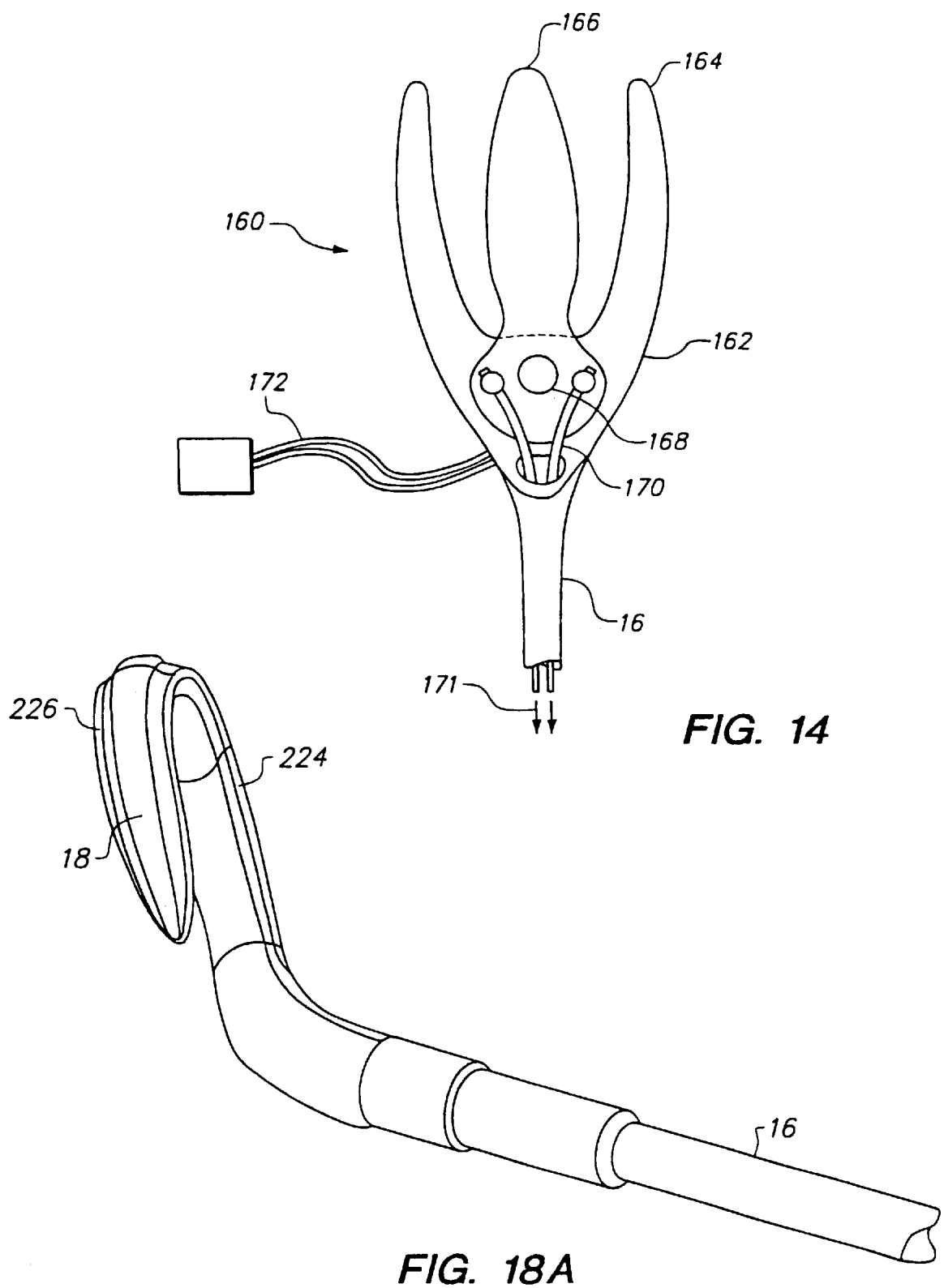
FIG. 14 shows an embodiment of the invention comprising a fork having an articulating finger and equipped with electrosurgical capability.
FIGS. 18A and 18B are perspective and top views respectively of an alternative curved or hooked configuration having exposed cautery wire means electrodes.

FIG. 14 depicts an embodiment 160 of the invention comprising a fork 162 having an articulating finger 166. In the illustration of FIG. 14 inner finger 166 is pivotally connected to fork 162 by means of pivot bearing 168 and toggles either right or left to engage an outer stationary finger 164. Alternatively outer fingers may pivot to engage an inner finger. For purposes of illustration only, articulating finger 166 may be actuated by cable mechanism 170. Pulling on the right-hand cable as illustrated by the arrows 171 pivots articulating finger 166 to the right, and pulling on the left-hand cable pivots articulating finger 166 to the left. Other actuating mechanisms, such as push rods, may alternatively be employed. Fingers 164 and 166 may include cutting blade edges, clamping jaws, or grasping surfaces. Embodiment 160 may comprise only mechanical elements, or may provide for unipolar or bipolar electrosurgery by means of electrical leads 172 connected to a suitable energy source. For example articulating finger 166 may be electrically insulated from stationary fingers 164 and connected to a unipolar electrical energy source by means of electrical leads 172, or articulating finger 166 may be electrically insulated from stationary fingers 164 with fingers 166 and 164 connected respectively to opposite poles of a bipolar electrical energy source by means of electrical leads 172. Those skilled in the art will recognize that alternative electrode arrangements may be used with the present invention.

Embodiment 160 can function as an electrosurgical fork 162 with all mechanically stationary fingers 164. One or more fingers 164 may be configured with cutting edges and connected to unipolar or bipolar energy sources. In this configuration the electrically active fingers may serve as electrosurgical cutting or coagulating ("Bovie") knives. In a configuration comprising one or more articulating fingers 166, embodiment 160 can function as electrosurgical scissors, wherein the knife edge of one finger engages another finger.

In operation embodiment 160 may be used to capture, engage, manipulate, clamp, coagulate, and cut vessels such as the IMA and side branches, tubular body organs, and related tissue. Use of embodiment 160 to coagulate and cut potentially eliminates the need for a separate electrosurgical knife, thereby reducing the number of instruments in the minimal operating field and thus increasing visibility and freedom of motion therein. When used alone or in combination with electrically insulated instruments embodiment 160 reduces the risk of accidental electrical shock or unwanted electrosurgical effects. Use of embodiment 160 further potentially reduces the need to apply mechanical surgical clips to side branches, thereby reducing the time for a procedure involving application and removal of mechanical clips, and reducing the risk of misplaced or lost mechanical surgical clips within the patient? body. A vessel or side branch can be woven and captured through the spaces between fingers 164 and 166, thereby exposing a greater length of vessel or side branch to coagulating energy, and insuring complete cauterization prior to cutting.

In a manner equivalent to that of the embodiment 160 of FIG. 14, various alternative embodiments of an electric cautery member having a hooked or curved configuration are illustrated in FIGS. 15 through 31, and provide a specialized electrosurgical instrument in accordance with the invention for capturing, manipulating, cauterizing, and severing vessels, other elongated bodily structures and connective tissue. To this end, FIGS. 15A and 15B illustrate a basic embodiment of an electrically energized cautery loop instrument, including handle 14 and rod 16 secured at its proximal end to the distal end of the handle. The distal end of the rod 16 is formed in a hook or curved configuration 18 of selected configuration for engaging, manipulating and harvesting vessel 26. The curved configuration 18 includes a groove formed within the top and leading surfaces along a major portion thereof for confining therein a cautery electrode in the form of a wire 200. The rod 16 includes a lumen therein (not shown) through which an electrical conductor supplies electrical current to the cautery wire 200 from a suitable energy source (such as the source depicted in FIG. 14) via an electrical cord 202 and an on/off switch 204 in the handle 14. As illustrated by a line 205, the handle 14 and rod 16 are configured so that the handle is in-line with the working area of the curved configuration 18, that is, the upper surface of the curve containing the wire 200.

The FIGS. 16A and 16B illustrate alternative curved configurations 18 for the cautery curved configuration electrosurgical instrument of FIGS. 15A, 15B. FIG. 16A shows the curved configuration 18 formed at a 30 to 40 degree angle to the rod 16. FIG. 16B shows the curved configuration 18 at generally right angle to the rod 16. The curved configuration 18 in FIGS. 15A, 15B has no angle but is generally formed in-line with the rod 16. Thus, the invention intends that the curved configuration 18 can be formed at various angles and arc lengths, i.e. an arc of selected length.

FIGS. 17A and 17B illustrate in further detail a modification of the cautery curved configuration of FIGS. 15A, 15B, and includes handle 14 formed, for example, of a stainless steel tube 206 suitably insulated by means of a plastic shrink tube 208 disposed about the tube 206. Only a portion of the handle 14 is shown. A curved configuration 18 formed of a suitable high temperature insulating material is secured along a straight portion 210 within the distal end of the tube 206, with the curved configuration 18 thereof extending from the handle. In accordance with the invention, a cautery electrode in the form of a wire 212 extends through the tube 206 and a lumen in the straight portion 210 of the curved configuration. The cautery wire 212 then is confined in a groove 214 (FIG. 17B) in the top and leading surfaces of the curved configuration 18. The distal end of the cautery wire is secured within the tip 19 of the curved configuration 18 as depicted at 216. A nonconductive disk 218 secured within the tube 206 and to the cautery wire 212 provides a shoulder for one end of a spring 220, the other end of which is confined by the end of the straight portion 210. The force of the spring 220 against the disk 218 imparts tension to the cautery wire 212 to maintain it in place in the groove 214 during a harvesting procedure. As depicted in FIGS. 15 and 17, the cautery curved configuration instrument is connected to a unipolar energy source.

The cautery electrode of FIGS. 17A, 17B, as well as any of the electrodes of further description hereinafter, may be formed of various electrically conductive materials such as, for example, stainless steel, nickel chromium alloy, nickel titanium alloy, titanium, etc.

Figure 18B:
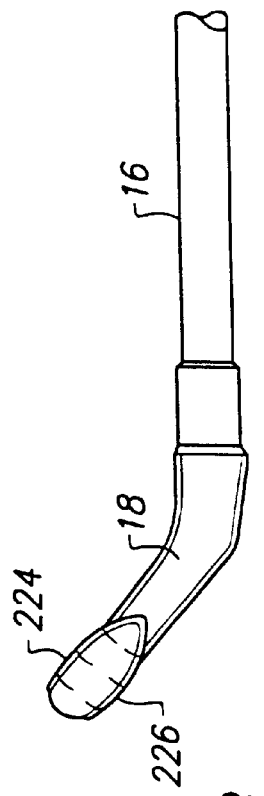

FIGS. 18A and 18B illustrate a configuration of the present invention wherein the curved configuration 18 is formed at a selected angle to the rod 16, such as previously illustrated in FIG. 16A. In FIGS. 18A, 18B the curved configuration 18 is provided with a pair of cautery electrodes in the form of wires 224 and 226 embedded in opposite side surfaces of the curved configuration. The wires 224, 226 could be replaced with cautery ribbons. As in FIGS. 15–17, the cautery wires 224, 226 are exposed along the major portion of the curved configuration to provide electrical contact with connecting tissue and side branches as the instrument is advanced or retrieved along the vessel being harvested. The curved configuration of FIGS. 18A, 18B is particularly useful in harvesting vessels which extend parallel to the center line of the handle and rod of the instrument, as when harvesting the LIMA through a xyphoid or sub-xyphoid incision.

Figure 19B:
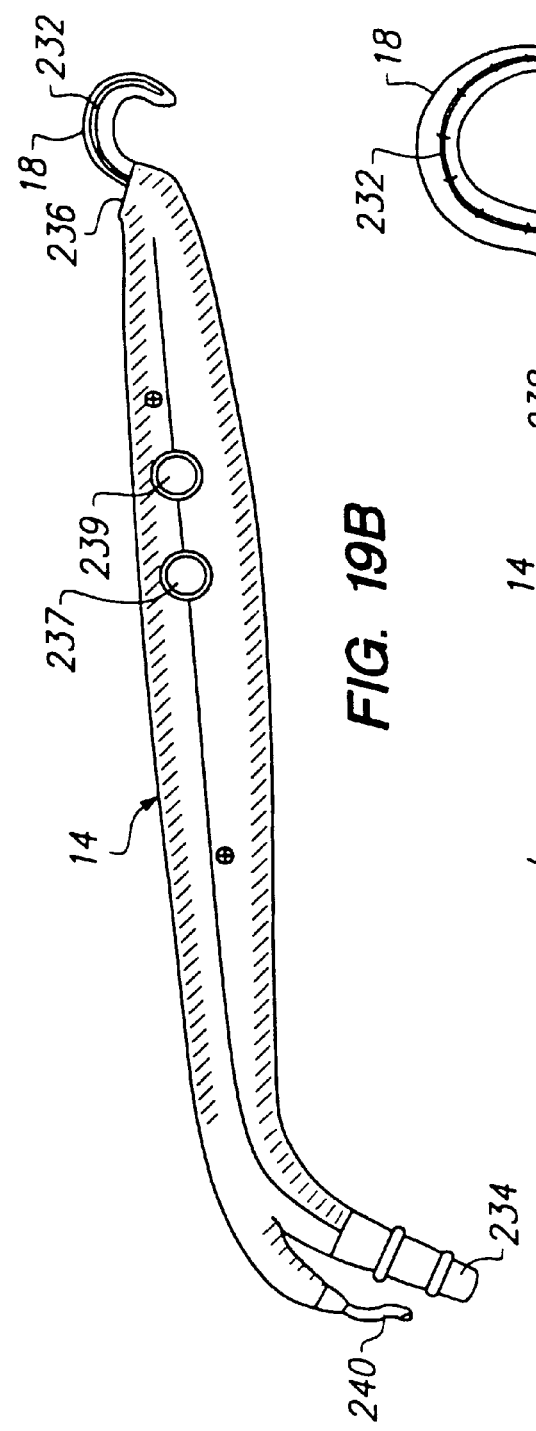
FIGS. 19A and 19B are a perspective and side view, respectively, illustrating a specialized surgical instrument of the invention including an electric cautery curved configuration and smoke evacuation means.
Figure 19A:
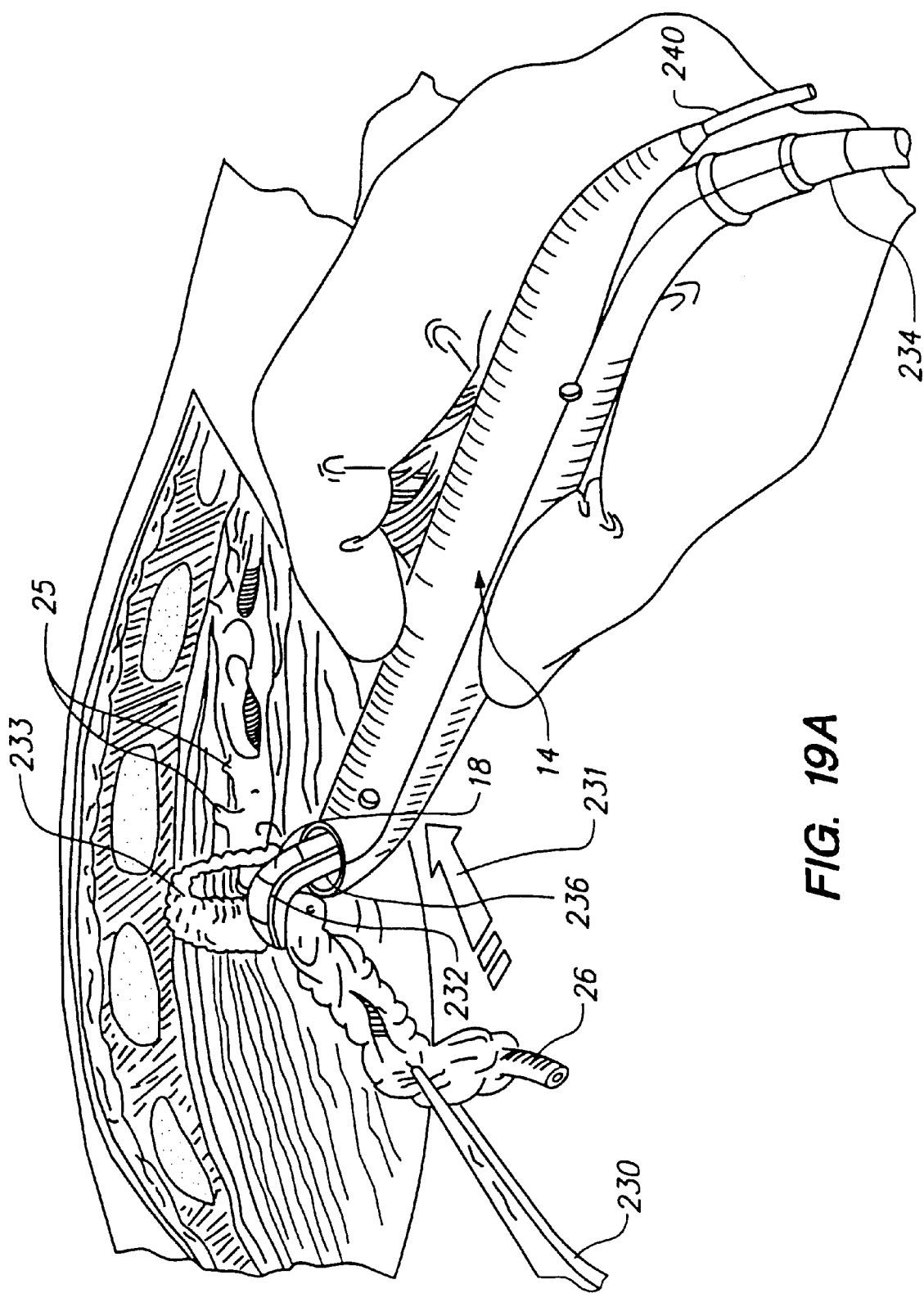

FIGS. 19A, 19B illustrate an alternative embodiment of an electrosurgical instrument of the invention, generally similar to those of FIGS. 15 and 17. FIG. 19A illustrates the embodiment in use harvesting a vessel 26 such as the LIMA or other elongated bodily structure or tissue. The embodiment in FIGS. 19A, 19B includes handle 14 which extends distally to the working area of the cautery curved configuration 18. As illustrated, a surgeon gently manipulates the vessel 26 to disengage it from surrounding tissue. In particular, the body of the curved configuration 18 acts as a spreading means which applies tension to the tissue being divided and which insulates nearby tissue and in particular the vessel 26 itself from the electrosurgical action and the heat of the cauterizing element. It this example, the vessel is also grasped with a pair of forceps 230 while the cautery hook instrument spreads, tensions and manipulates the vessel 26 when urged as depicted by arrow 231, to sever and cauterize side branches 25 and connective tissue using an exposed cautery electrode (depicted here as a wire) 232 contained in the side surface of the curved configuration 18. The process of cauterizing and cutting of tissue and side branches generates substantial smoke 233 which impairs visualization of the working area. Thus, the embodiment of FIGS. 19A, 19B also includes a suction lumen 234 which extends within the handle 14 to terminate in a suction port 236 in the working-area, thereby defining a smoke evacuation means integral with the instrument. To further facilitate visualization of the working area, the embodiment also may include a fiberoptic light 238 (FIG. 20) within the handle 14 with the light lens disposed to illuminate the working area The light is supplied via a suitable fiberoptic light guide (not shown) also housed in the handle 14. Electrical current is provided to the cautery wire 232 from a suitable energy source via a pair of button switches 237, 239 embedded in the handle 14 and an electrical cord 240 (FIG. 19B). The button switches supply suitable electrical energy for separately selecting the process of coagulation or severing of side branches and tissue. Button switches 237, 239 and cord 240 replace the switch 204 and cord 202 previously depicted in FIG. 15A.

Figure 20:
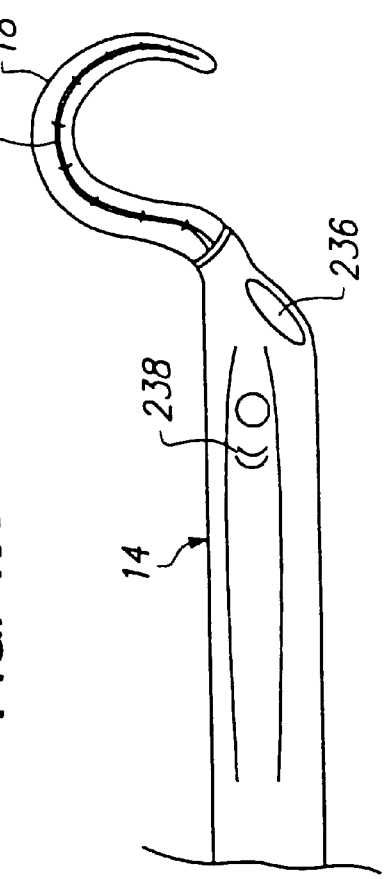
FIG. 20 is an elevational view of the distal working end of the cautery curved configuration instrument of FIGS. 19A, 19B, further depicting light means.

FIG. 20 illustrates the working end of the instrument similar to that in FIGS. 19A, 19B, including a distal portion of the handle 14 and a curved configuration 18 having the cautery electrode or wire 232 suitably embedded or otherwise attached to the side surface of the curved configuration. Suction is provided via the suction or smoke evacuation port 236, and light is provided via the fiberoptic light 238. The curved configuration 18 may be adapted for removal so that it may be replaced if desired. Suitable mating electrical contacts (not shown) are provided between the curved configuration and the associated distal end of the handle 14. As previously mentioned, the wires 232 could be replaced by embedded ribbons, or by the cautery coils of description below.

Figure 21:
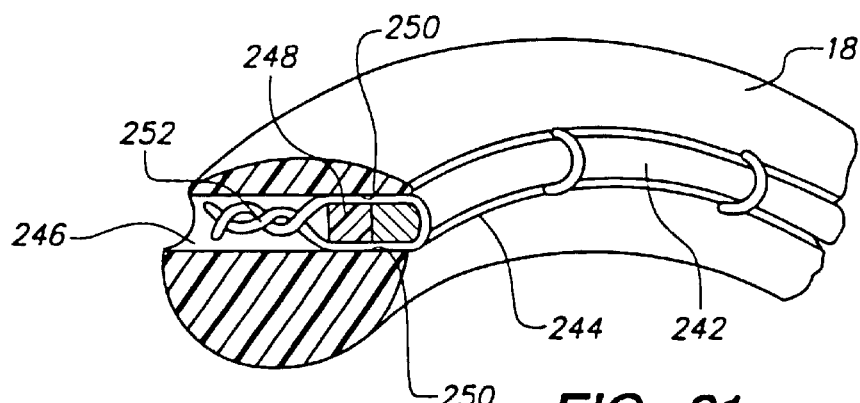
FIG. 21 is a perspective view of a cross section and portion of a curved configuration illustrating means for securing an exposed cautery wire within a selected surface of the curved configuration.

FIG. 21 illustrates means for securing a cautery electrode in the form of a wire 242 within a groove 244 in a curved configuration 18, while allowing the wire to be exposed along the length of the groove and curved configuration. To this end, a spaced series of counterbores 246 are formed, drilled, etc., through most of the curve cross-section in register with the groove 244 but leaving intact a portion 248 of the cross-section which abuts the wire 242. A pair of wire-size bores 250 are formed or drilled at opposite sides of the diameter of the counterbore 246, which bores penetrate into the groove 244 at opposite sides of the cautery wire 242. A tie wire 252 is disposed about the cautery wire 242, with the ends inserted through the wire-size bores 250 and twisted together a short length so as to be buried in the respective counterbores 246. The series of tie wires 252 thus confine the cautery wire 242 within the groove 244. The tie wires 252 may be tightly or loosely twisted. If loosely twisted, the tie wires allow axial or rotational movement of the cautery wire 242 with respect to the tie wires 252 and the groove 244. This in turn provides means for cleaning or otherwise removing residual, charred, coagulated, entangled, etc., tissue and blood from the cautery wire 242. Examples of such selfcleaning cautery wire embodiments are further discussed below.

Figure 22D:
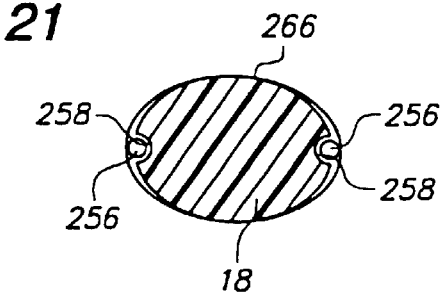
FIG. 22D is a cross-sectional view of the invention of FIG. 22A illustrating an alternative cautery electrode confining means of the invention.
Figure 22A:
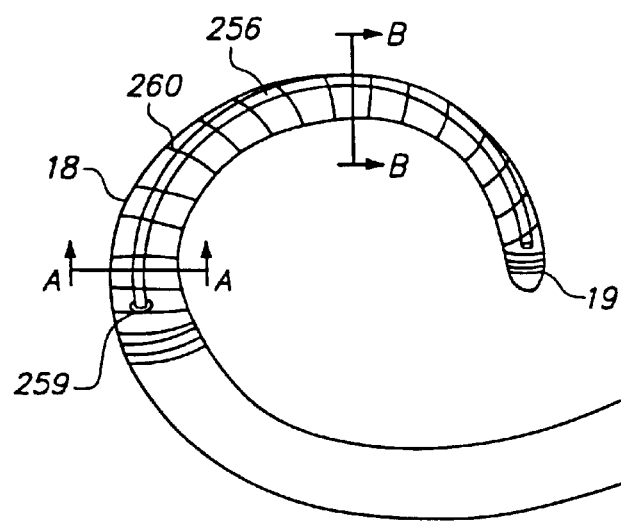
FIG. 22A is an elevational view illustrating an alternative means for securing or confining an exposed cautery wire to a curved configuration.
Figure 22C:
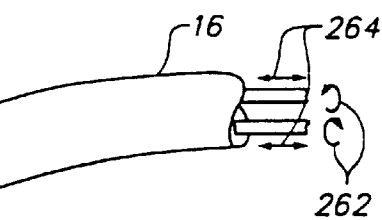
FIGS. 22B and 22C are cross-sectional views taken along section lines A—A and B—B respectively of FIG. 22A.
Figure 22B:
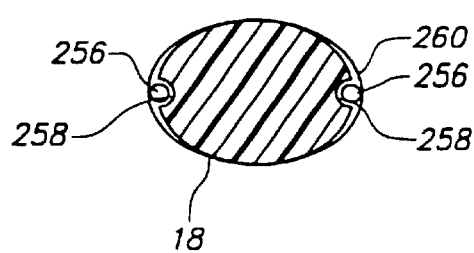

FIGS. 22A, 22B, 22C and 22D show alternative embodiments of a cautery curved configuration of the invention illustrating other means for confining a pair of exposed cautery electrodes or wires 256 in respective grooves 258 (FIGS. 22B, 22C) in the curved configuration 18. The confining means also can be used with a curved configuration having only one cautery wire. The curved configuration 18 is integrally formed with the rod 16, in a selected configuration and angle such as disclosed here and in the other Figures. Conductors leading to the exposed cautery wires, or the cautery wires themselves, are embedded in the rod 16 or extend through a lumen therein. The cautery wires 256 are exposed via respective holes 259 at either side of the curved configuration 18 and extend therefrom within respective grooves 258 to the tip 19 of the curved configuration. As more clearly shown in the cross-sectional FIGS. 22B, 22C, the grooves 258 and thus the cautery wires 256 exit the curved configuration 18 at opposite sides thereof as depicted in FIG. 22B. The grooves gradually converge as they reach their midpoint in the region depicted in FIG. 22C, where the grooves 258 merge into a single wider groove and the cautery wires 256 extend side-by-side therein. The grooves and wires gradually diverge back to the opposite sides of the curved configuration at the tip 19 thereof. In this way, the position of the wires, and thus the direction of their exposure and the associated cutting and coagulating action of the instrument can be controlled. In this case, the cautery wire is further from the vessel which would generally be located inside the curved configuration 18 in the central section thereof, i.e. in the region of the section B—B, FIG. 22A.

The wires 256 are retained in place in respective grooves 258 by a specially wrapped non-conductive line or thread 260 extending from prior to the exit holes 259 of the cautery wires to the tip 19 of the curved configuration. The cautery wires 256 can be rotated in place as depicted by arrows 262 to rotate the wires in their respective grooves thereby providing a self-cleaning action against the groove edges. Alternatively, or simultaneously, the wires 256 can be reciprocated longitudinally as depicted by arrows 264 to provide the self-cleaning action as they pass under the confining turns of the thread 260.

FIG. 22D illustrates an alternative electrode confining means, namely, tie wires 266 in the form of individual rings spaced at selected intervals along the length of the curved configuration 18, and secured about the circumference of the configuration and cautery electrodes to contain the electrodes in their respective grooves. Such individual tie wires 266 may be employed with any of the embodiments of description herein.

A mechanism for imparting the reciprocating movement to the cautery wire generally includes a stiff control wire extending through the handle 14 and attached at its proximal end to a spring loaded lever mounted in the handle. The spring maintains the cautery wire in a nominal position. Application of force on the lever overcomes the spring force and moves the cautery wire a selected distance to a second position. Rotation of the cautery electrode may include a slow speed motor housed in the handle 14 with an additional speed reducing gear arrangement coupled to a stiff wire. The cautery electrode wire (or coil) is suitably coupled to, but insulated from, the stiff wire, and is rotated upon the motor being energized.

Figure 23:
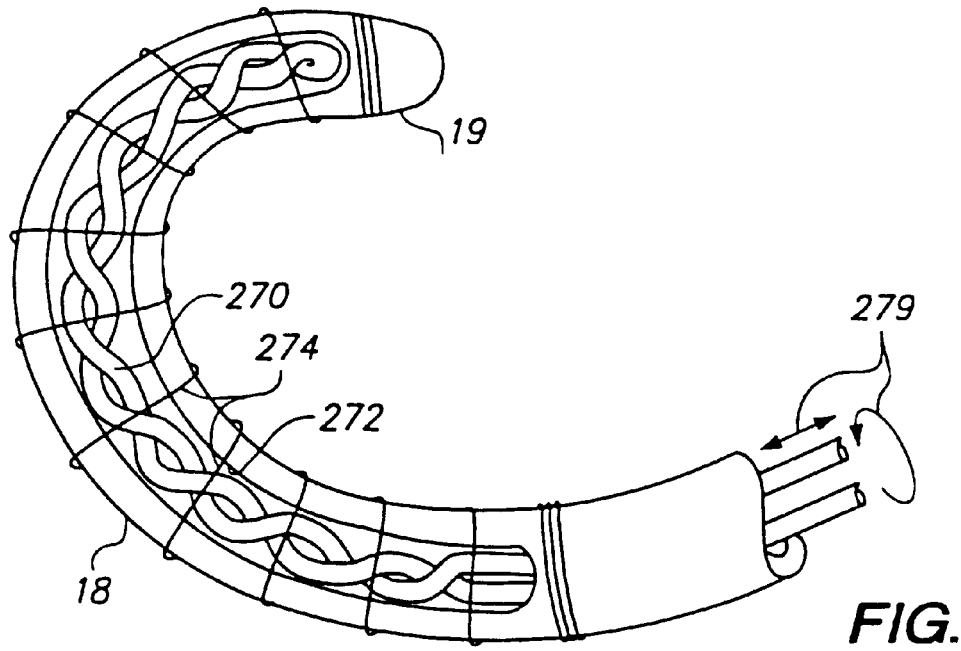
FIG. 23 is an elevational view illustrating an alternative exposed cautery wire means using a twisted wire electrode configuration.

FIG. 23 illustrates a further alternative embodiment of a cautery curved configuration employing a twisted, braided, etc. cautery electrode in the form of wire means 270 confined in a shallow groove 272 formed in a selected length of the curved configuration 18. The cautery wire means 270 is confined in the shallow groove 272 by means of a spirally wrapped line or thread 274 extending over and beyond the length of the groove 272, in a configuration similar to the confining means of FIG. 22A. The twisted or braided cautery wire means 270 is exposed to surrounding tissue or side branches to provide the process of cutting and cauterizing.

Figure 24A:
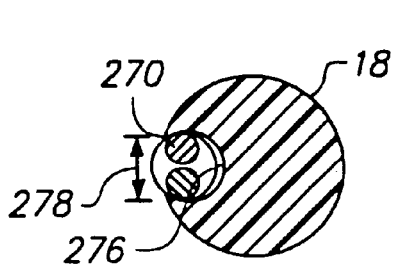
FIG. 24A is a cross-sectional view of the curved configuration and cautery electrode configuration of FIG. 23, but using an alternative means for containing the electrode within the surface of the curved configuration.

In an alternative embodiment of FIG. 24A the spirally wrapped thread 274 is replaced by selectively confining the cautery wire means in a precisely sized groove 276. That is, the diameter of the groove 276 and its depth into the curved configuration 18 cross-section is selected relative to the outside diameter of the twisted or braided cautery wire means 270 so that a narrow strip 278 of the cautery wire means protrudes from the configuration along its length to thus be exposed for electrical contact with adjacent tissue and side branches, while still being positively contained within the groove 276 as illustrated for example in FIG. 24A.

As in the embodiment of FIG. 22A, the twisted or braided cautery wire means 270 may be rotated or reciprocated within the groove 272 or 276 as depicted by the arrows 279, to provide the self-cleaning action of previous description. A mechanism for imparting rotating and/or reciprocating movement to the cautery wire is discussed above relative to FIG. 22A.

Figure 24B:
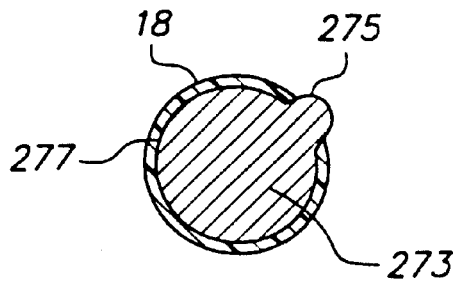
FIG. 24B is a cross-sectional view of an alternative embodiment of a cautery electrode/curved configuration combination.

FIG. 24B illustrates a further embodiment of a cautery electrode/curved configuration, wherein the major cross-section of the curved configuration 18 is formed by an electrically conductive cautery electrode 273. A protrusion 275 is formed which extends a selected length of the curved configuration and provides electrical contact with side branches and connective tissue. An insulating coating 277 is formed over the remaining cylindrical surface to insulate the curved configuration 18.

Figure 25:
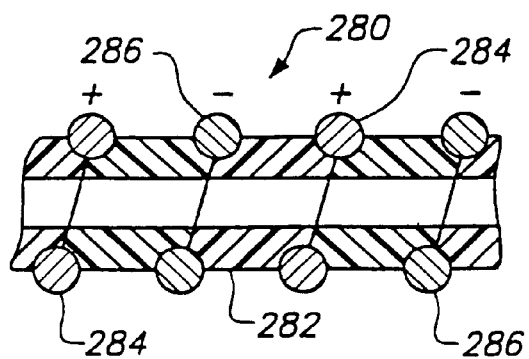
FIG. 25 is a cross-sectional view of a portion of a cautery electrode, illustrating a bipolar electrode configuration.

FIG. 25 illustrates a bi-polar coil configuration 280 for use in a cautery curved configuration in place of the various cautery wire configurations disclosed in the previous FIGS. 15–24 which, in general, depict a unipolar cautery wire configuration. The coil 280 is formed of a support tube 282 of a suitable insulating material, and selectively spaced wraps of a pair of coils 284, 286 which are partially embedded in the outer cylindrical surface of the insulating tube 282. Coils 284 and 286 conduct electricity of opposite polarities to provide a bipolar cautery action between the coils.

Figure 26A:
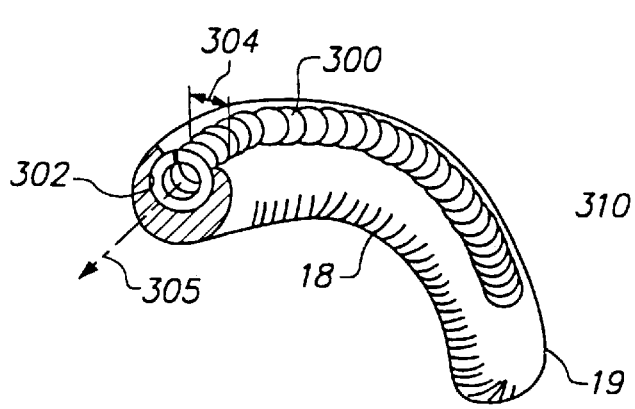
FIGS. 26A through 26E are perspective views of portions of respective curved configurations illustrating several alternative embodiments of electric cautery curved configurations using a coil electrode.

FIGS. 26A–26D show portions of a curved configuration 18 illustrating various alternative embodiments of cautery electrodes formed of coils rather than the wires or ribbons of previous description. FIG. 26A illustrates an electrically energized cautery coil 300, a major cross-section of which is embedded in a matching groove 302. A portion of the coil 300 along its length is exposed to provide an exposed strip 304 for electrical contact with adjacent tissue and side branches. The coil diameter is relatively large with respect to the diameter of the curved configuration 18 and the groove is configured so that the coil 300 is confined within the configuration in the manner described in FIG. 24A, thereby dispensing with the tie wires or spirally wrapped threads, etc., of FIGS. 21, 22, 23. As previously described, the coil 300 may be rotated or reciprocated to provide the self-cleaning action. In addition, since the coil forms in effect a continuous tube the sides of which are permeable to air, fluids, etc., the coil 300 may be used as a vacuum tube to provide smoke evacuation or a flood of fluid as depicted by arrow 305 and described in FIG. 19.

By way of example only, a cautery electrode in the form of a coil such as described in FIGS. 26A–26D may be made of 0.010 inch diameter wire, wherein the wound coil measures 0.049 inch outside diameter. If the groove in which the 0.049 coil is embedded is of the order of 0.045 inch diameter, then the coil will be confined within the groove even when the coil is under considerable torque as when being rotated. See the wire electrode 270 and groove 276 of FIG. 24A.

Figure 26B:
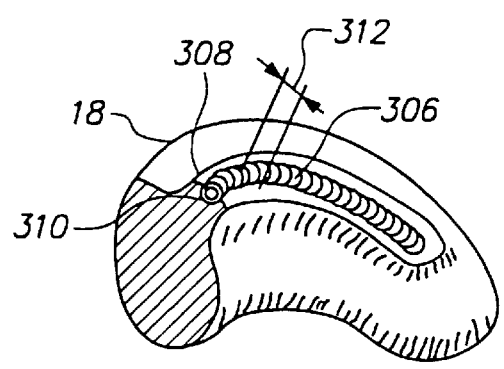

FIG. 26B illustrates a cautery coil electrode wherein a coil 306 is of smaller diameter relative to the diameter of coil 300 in FIG. 26A. The curved configuration 18 is provided with a protruding portion 308 along the working length of the configuration, and a groove 310 is formed within the protruding portion. As in FIG. 26A, the groove 310 is of a diameter and is located relative to the outer surface of the protruding portion 308, such that it confines the coil 306 within the curved configuration 18 while still exposing a strip 312 along the length of the coil to surrounding tissue and side branches. The coil 306 also may be used as a smoke evacuation tube and/or may be rotated or reciprocated to provide the self-cleaning action.

Figure 26C:
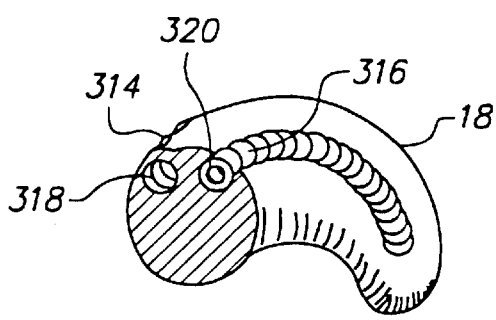

FIG. 26C illustrates an alternative embodiment of a cautery curved configuration 18 employing a pair of electrodes or coils 314,316 embedded in respective grooves 318, 320 in the manner described in FIGS. 26A or 26B. The dual coil configuration allows the cutting and cauterizing process to be performed while moving the cautery curved configuration in either direction, without having to rotate the instrument.

Figure 26D:
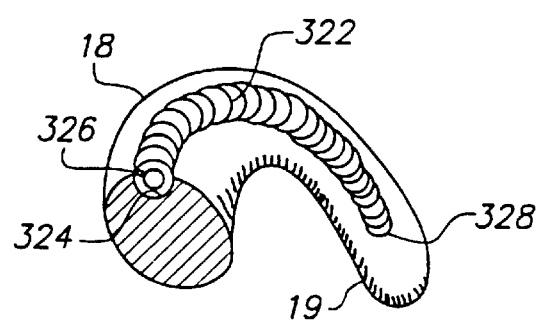

FIG. 26D illustrates another alternative embodiment of a curved configuration 18 wherein a coil 322 is embedded in a groove 324, wherein the groove and thus the coil location varies along the working length of the curved configuration 18. More particularly, the coil 322 may initially exit from the curved configuration 18 at a top location 326 of the configuration cross-section. The groove and coil location then transitions from the top location to terminate at the tip 19 at an inside location 328. Alternatively, the groove and coil may terminate at the front (leading) or side surface of the curved configuration 18 at the tip 19.

Figure 26E:
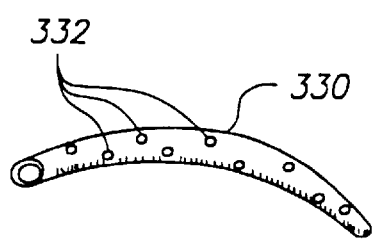

FIG. 26E illustrates a modification to the cautery coil electrode configurations of, for example, FIGS. 26A–26D. A small tube 330 formed of an insulating and flexible material is formed with perforations 332 along its length. The tube 330 has an outside diameter and length to allow it to be inserted into the coils 300, 306, 314, 316 or 322 of previous description. The tube 330 is used for example to meter fluid evenly in or out of the coil area over the entire length of the coil and thus of the working area of the cautery curved configuration 18. Thus the tube may be used for smoke or fluid evacuation, or may be used to supply a selected fluid evenly over the working area of the curved configuration.

Figure 27A:
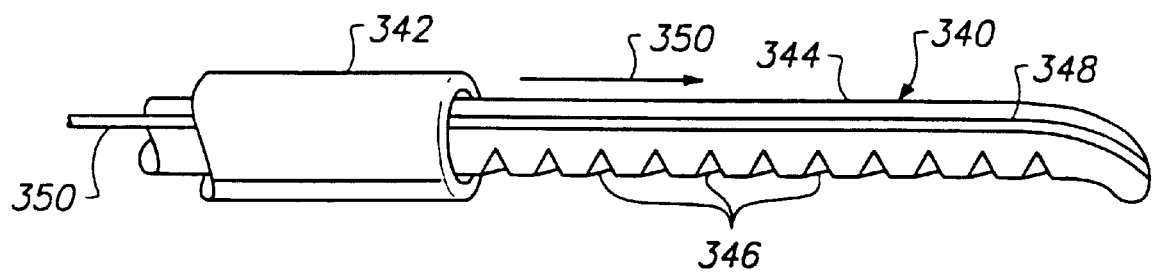
FIGS. 27A and 27B are perspective views illustrating an alternative embodiment of the invention including a retractable curved configuration formed of a material having an inherent shape-memory property.
Figure 27B:
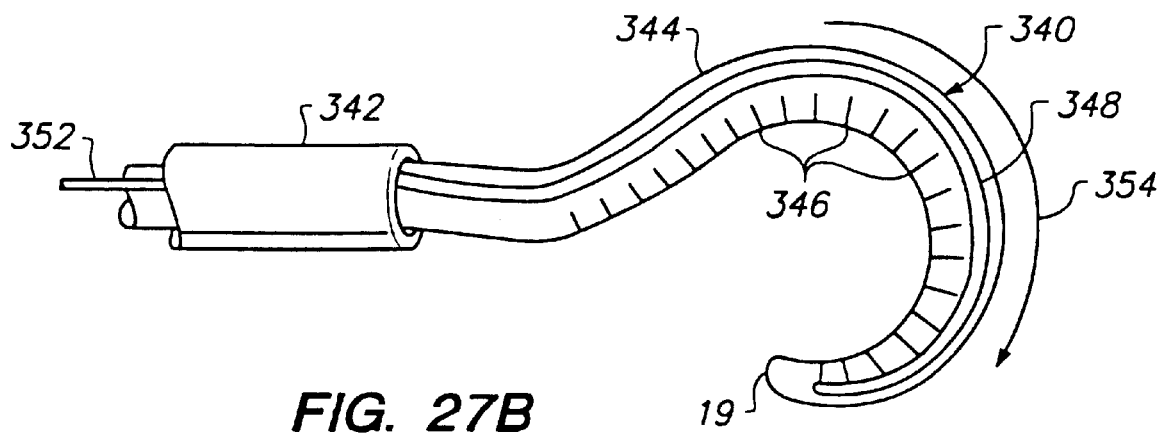

FIGS. 27A and 27B illustrate still another embodiment of the invention suitable for delivery through a trocar port positioned in the patient's thoracic cavity for endoscopic surgery. This embodiment employs a retractable distal working end, that is, a retractable cautery curved configuration 340, and includes a housing in the form of a tube 342 (only a distal portion is shown) which is coaxially formed or otherwise attached to a handle, such as shown in FIGS. 15, 17, 19. The cautery curved configuration 340 is formed of a rod 344 of flexible and electrically non-conductive material. The rod 344 is consecutively notched as at 346 to permit easier deformation thereof into a predetermined curved configuration. A wire 348 is embedded into the rod 344 and is formed, for example, of a nickel-titanium alloy material having an inherent shape-memory property. That is, once the material is pre-formed into a predetermined shape application of an associated electrical current will cause the material to return to its predetermined shape. The material thus is similar to that described in the invention embodiment of previous FIGS. 6–9. In this embodiment, the nickel-titanium alloy wire 348 in the working end of the rod 344 is preformed to define the predetermined curved configuration 340.

FIG. 27A depicts the rod 344 as it is being extended from the protective housing of the tube 342 (arrow 350). Upon full extension, application of an electrical current to the nickel-titanium alloy wire 348 by a suitable energy source (not shown) via a conductor 352, causes the pre-formed portion of the wire 348 in the working area to return to its predetermined curved configuration, as shown by arrow 354 in FIG. 27B.

Although a cautery electrode is not shown in the retractable embodiment of FIGS. 27A, 27B, it is to be understood that a cautery wire or coil may be embedded along the centerline surface of the rod 344 in the working area of the curved configuration 340 in the manner variously described in the previous FIGS. 15–26E.

Figure 28:
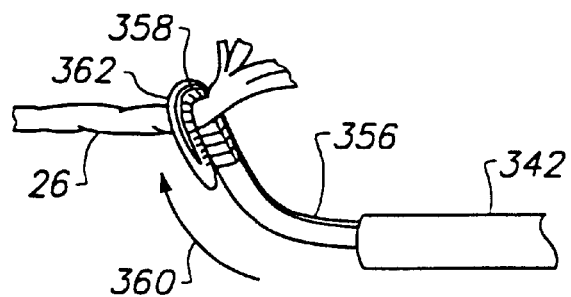
FIG. 28 is an elevational view illustrating an alternative retractable curved configuration of the FIGS. 27A, 27B.

FIG. 28 illustrates an alternative embodiment of the retractable curved configuration 340 of FIGS. 27A, 27b wherein a rod 356 similar to the rod 344 includes a nickel-titanium alloy wire 358 embedded in the working end thereof. In this embodiment the wire 358 is pre-formed into a predetermined configuration 362 which also is bent at a selected angle (arrow 360) relative to the center-line of the handle and housing tube 342. The added angle allows the instrument to be used in retrieval takedown procedures for a vessel 26 such as the LIMA when the vessel extends parallel to the center-line of the instrument. Such a curved configuration also is shown and described in previous FIGS. 18A, 18B.

Figure 29A:
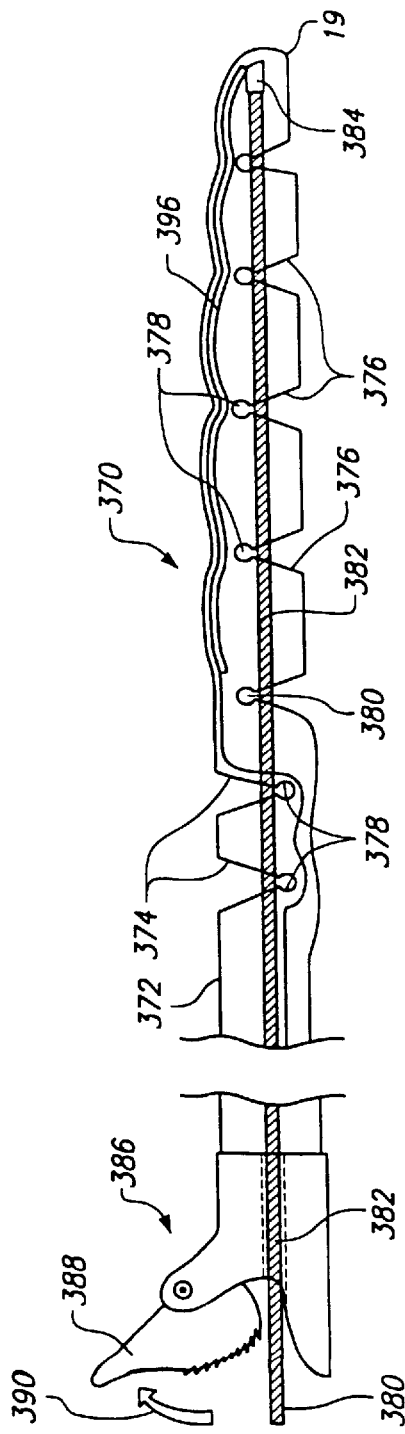
FIGS. 29A, 29B are side views illustrating another alternative pre-formed curved configuration of the invention.

FIGS. 29A through 31 illustrate a further alternative embodiment of the invention employing a pre-formed curved configuration 370 generally similar to the curved configuration 340 of FIGS. 27A, 27B, but wherein the curved configuration is established by means of selective notches and a pull-wire assembly. More particularly, the curved configuration 370 is formed of a rod 372 of flexible and electrically non-conductive material. The rod 372 is notched as at 374 in an upper portion thereof at the proximal end of the curved configuration 370 itself. The rod is also notched along the lower portion thereof for the length of the curved configuration 370, as indicated at 376. The notches 374 and 376 thus determine the eventual shape of the curved configuration 370. A relief bore 378 is formed through the rod cross-section at the apex of each notch 374, 376 to facilitate the desired bending of the rod into the curved configuration 370. A pull-wire 380 is embedded within a lumen 382 within the rod 372 along generally the centerline thereof. A distal end 384 of the pull-wire 380 is anchored at the tip 19 of the rod 372, that is, of the curved configuration 370. In FIGS. 29A, 29B the pull-wire 380 extends through the lumen 382 in the rod 372 to a locking mechanism 386 disposed here at the proximal end of the rod. The locking mechanism 386 includes a proximal end of the pull-wire 380 extends. A locking/unlocking cam 388 with wire-engaging serrations is pivotally secured in the mechanism above the pull-wire. When the cam 388 is raised to disengage it from the pull-wire (arrow 390, FIG. 29A) the pull-wire 380 may be translated within the lumen 382. To form the curved configuration 370 of FIG. 29B, the pull-wire 380 is pulled proximally (arrows 392), whereupon the cam 388 is pivoted down to engage the pull-wire (arrow 394) to lock the shape of the curved configuration 370. A cautery wire, ribbon, etc., electrode 396 is selectively contained by the curved configuration 370, as described in previous figures, to provide the cutting and cauterizing functions.

Figure 29B:
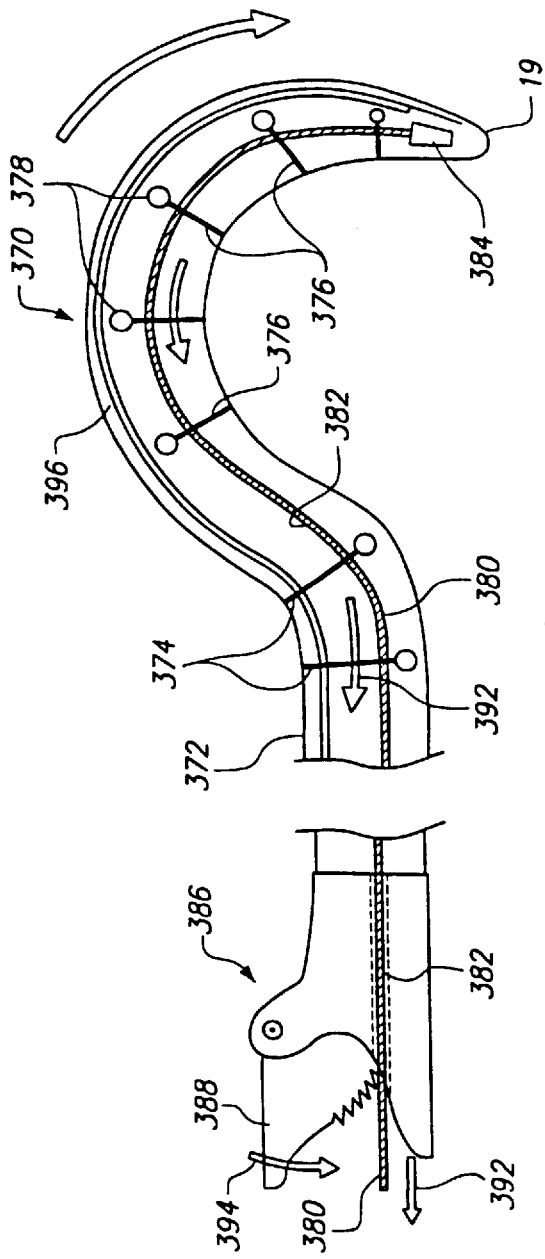
Figure 30:
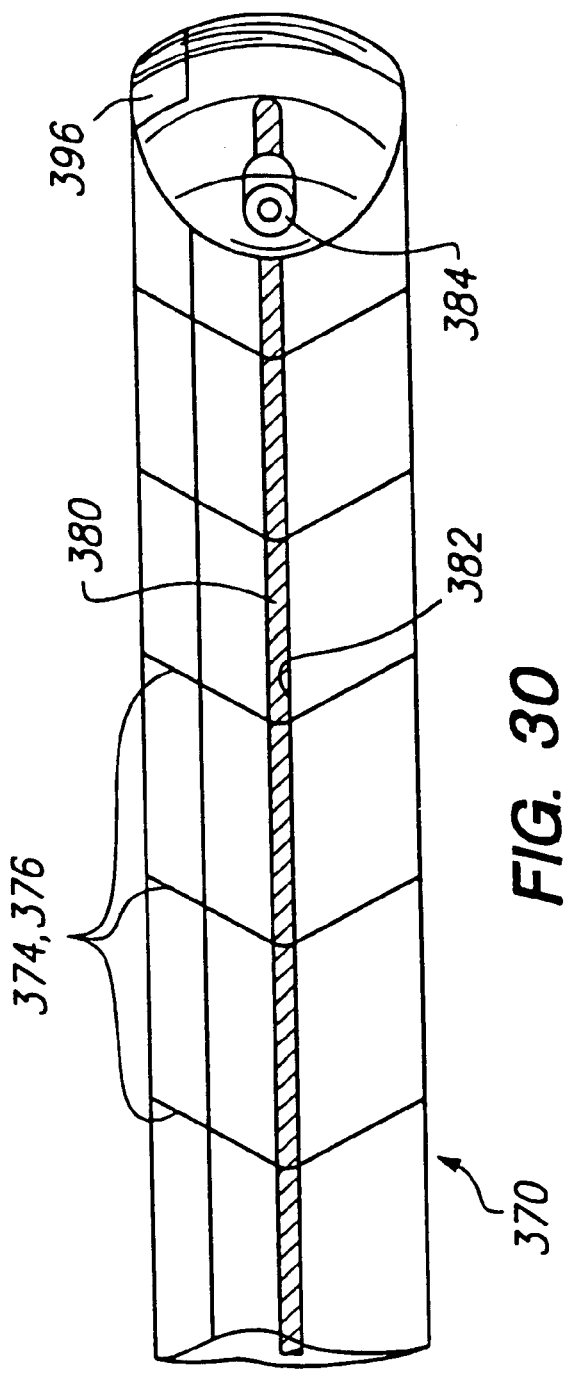
FIG. 30 is a bottom view illustrating a modification of the curved configuration of FIGS. 29A, 29B.

FIG. 30 illustrates a modification to the notch configuration of the previous FIGS. 27A–29B wherein the notches 374 and/or 376 are provided with an interlocking V-groove configuration to increase the lateral stability of the curved configuration 370 when locked in place.

Figure 31:
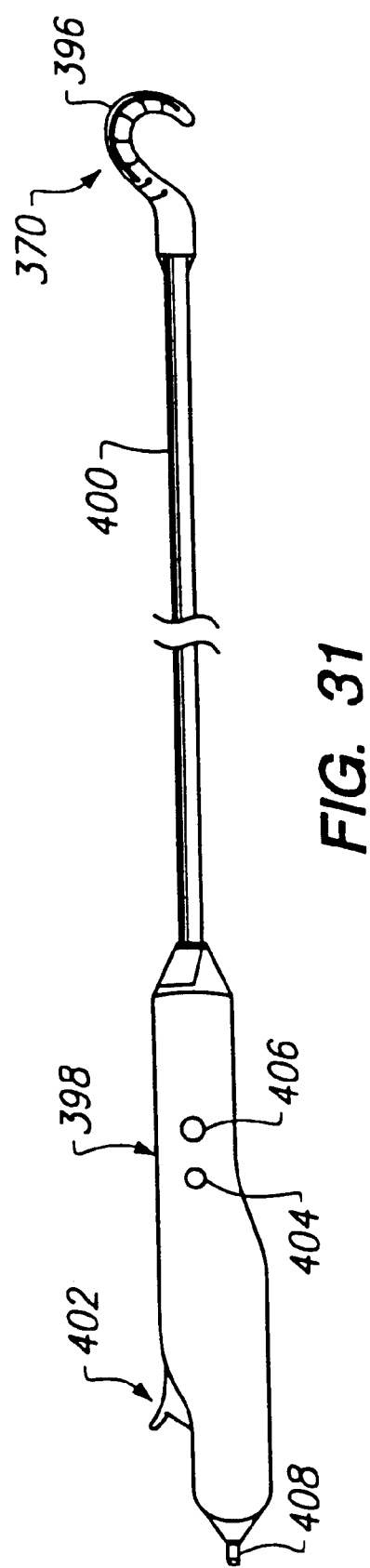
FIG. 31 is a side view of an alternative embodiment of an electrosurgical instrument embodying the curved configuration of FIGS. 29A, 29B, and 30.

FIG. 31 illustrates an alternative embodiment of a curved configuration electrosurgical instrument in accordance with the invention embodying the features of FIGS. 29 and 30. The instrument includes a handle 398, equivalent to the handle 14 of FIGS. 15A, 17A, 19A, 19B and 20, and coupled at its distal end to a preferably malleable, elongated shaft 400. The curved configuration 370 of FIGS. 29, 30 is secured to, or formed with, the distal end of the shaft 400. The pull-wire 380 extends within the length of the shaft and through the handle 398 to terminate at a locking mechanism 402 the equivalent of the mechanism 386 of FIGS. 29A, 29B. The locking mechanism 402 also includes means for pulling the attached pull-wire 380 into the handle 398 prior to locking the pull-wire, and thus the curved configuration 370, in place. The cautery electrode 396 is electrically energized by means of an electrical conductor extending therefrom through the shaft 400, and a pair of electrical button switches 404, 406 similar to the switches 237, 239 of FIG. 19B. Suitable electrical energy is supplied to the switches 404, 406 via an electrical cord 408 extending from the proximal end of the handle 398. The malleable shaft 400 allows the instrument to be bent into a desirable shape.

Although the invention has been described herein relative to specific embodiments, various additional features and advantages will be apparent from the description and drawings, and thus the scope of the invention is defined by the following claims and their equivalents.

What is claimed is:
1. A method of manipulating a vessel within bodily tissue exposed through an incision using a surgical instrument having a curved vessel-engaging segment and including electrical insulation on the curved segment and an electrosurgical electrode disposed thereon, the method comprising:
    detaching an initial portion of the vessel from adjacent tissue;
    atraumatically spreading and pulling successive portions of the length of the vessel from its native tissue bed with the curved segment of the instrument;
    engaging the initial portion of the vessel with the curved segment of the instrument to detach adjacent tissue from additional portions of the length of the vessel;
    manipulating the electrosurgical electrode disposed on the curved segment of the instrument into operative engagement with connective tissue or side branches;
    selectively electrically energizing the electrode to effect severing or cauterizing of tissue in operative engagement therewith; and
    advancing the instrument along the vessel to sever or cauterize side branch vessels encountered during detachment of additional portion of the length of the vessel from adjacent tissue.
2. A method of manipulating a vessel within bodily tissue exposed through an incision using a surgical instrument having a curved vessel-engaging segment and including an electrosurgical electrode and electrical insulation on a portion thereof disposed to contact a vessel, the method comprising:
    detaching an initial portion of the vessel from adjacent tissue;
    engaging the initial portion of the vessel with the curved segment of the instrument to detach adjacent tissue from additional portions of the length of the vessel;
    electro-cauterizing tissue in response to electrical signal applied to the electrode;
    insulating the vessel from electrical signal selectively applied to the instrument to provide electro-cauterization;
    advancing the instrument along the vessel to sever or cauterize side branch vessels encountered during detachment of additional portions of the length of the vessel from adjacent tissue; and
    selectively manipulating the electrosurgical electrode relative to the curved segment for self-cleaning the electrode.
3. A method of manipulating a vessel within bodily tissue exposed through an incision using a surgical instrument having a curved vessel-engaging segment and including an electrosurgical electrode and electrical insulation on a portion thereof to contact a vessel, the method comprising:
    confining the electrosurgical electrode within a groove in the curved segment of the instrument with a selected portion of the electrode exposed;
    detaching an initial portion of the vessel from adjacent tissue;
    engaging the initial portion of the vessel with the curved segment of the instrument to detach adjacent tissue from additional portions of the length of the vessel; and
    advancing the instrument along the vessel to sever or cauterize side branch vessels encountered during detachment of additional portions of the length of the vessel from adjacent tissue.

4. A method of manipulating a vessel within bodily tissue exposed through an incision using a surgical instrument having a curved vessel-engaging segment, the method comprising;

detaching an initial portion of the vessel from adjacent tissue;

engaging the initial portion of the vessel with the curved segment of the instrument to detach adjacent tissue from additional portions of the length of the vessel;

advancing the instrument along the vessel to sever or cauterize side branch vessels encountered during detachment of additional portions of the length of the vessel from adjacent tissue; and transferring selected fluid with respect to a surgical site of severing or cauterizing tissue via a conduit in the curved segment of the instrument.

5. A method of manipulating a vessel within bodily tissue exposed through an incision using a surgical instrument having a curved vessel-engaging segment, the method comprising;

detaching an initial portion of the vessel from adjacent tissue:

engaging the initial portion of the vessel with the curved segment of the instrument to detach adjacent tissue from additional portions of the length of the vessel;

advancing the instrument along the vessel to sever or cauterize side branch vessels encountered during detachment of additional portions of the length of the vessel from adjacent tissue; and delivering radiant flux to a surgical site of severing or cauterizing tissue via fiberoptic channel integral with the curved segment of the instrument.

\* \* \* \* \*